(12) United States Patent
Kasamatsu et al.

(10) Patent No.: US 10,119,892 B2
(45) Date of Patent: Nov. 6, 2018

(54) AUTOMATIC TISSUE STAINING DEVICE AND AUTOMATIC TISSUE STAINING METHOD

(71) Applicant: NICHIREI BIOSCIENCES INC., Tokyo (JP)

(72) Inventors: Toshiyuki Kasamatsu, Tokyo-to (JP); Noboru Horikoshi, Tokyo-to (JP)

(73) Assignee: NICHIREI BIOSCIENCES INC., Tokyo (JP)

( * ) Notice: Subject to any disclaimer, the term of this patent is extended or adjusted under 35 U.S.C. 154(b) by 0 days.

(21) Appl. No.: 15/511,481

(22) PCT Filed: Sep. 18, 2015

(86) PCT No.: PCT/JP2015/076755
§ 371 (c)(1),
(2) Date: Mar. 15, 2017

(87) PCT Pub. No.: WO2016/047625
PCT Pub. Date: Mar. 31, 2016

(65) Prior Publication Data
US 2017/0292899 A1 Oct. 12, 2017

(30) Foreign Application Priority Data
Sep. 22, 2014 (JP) ................................ 2014-193026

(51) Int. Cl.
*G01N 1/00* (2006.01)
*G01N 1/31* (2006.01)
*G01N 35/00* (2006.01)

(52) U.S. Cl.
CPC ....... *G01N 1/312* (2013.01); *G01N 35/00029* (2013.01); *G01N 35/0095* (2013.01);
(Continued)

(58) Field of Classification Search
CPC ....................................................... G01N 1/00
See application file for complete search history.

(56) References Cited

U.S. PATENT DOCUMENTS 5,355,439 A 10/1994 Bernstein et al.
5,675,715 A 10/1997 Bernstein et al.
(Continued)

FOREIGN PATENT DOCUMENTS

JP 8-506888 7/1996
JP 2002-507738 3/2002
(Continued)

OTHER PUBLICATIONS

International Search Report dated Dec. 22, 2015 in International Application No. PCT/JP2015/076755.
(Continued)

*Primary Examiner* — Jyoti Nagpaul
(74) *Attorney, Agent, or Firm* — Wenderoth, Lind & Ponack, L.L.P.

(57) ABSTRACT

An automatic tissue staining device includes a supply head that supplies a treatment fluid, a horizontal direction movement unit that moves the supply head in a horizontal direction, and a holding unit that holds a plurality of glass slides on which samples are set. The automatic tissue staining device further includes a control unit that judges an occupancy status of the horizontal direction movement unit in a condition that one or more of the glass slides are situated in a first region prior to supplying the treatment fluid from the supply head to one or more samples in the first region, suspends a start of a treatment for the samples in the first region when the horizontal direction movement unit is occupied, and permits the treatment for the samples in the first region when the horizontal direction movement unit is not occupied.

20 Claims, 16 Drawing Sheets

(52) U.S. Cl.
CPC .......... *G01N 35/00722* (2013.01); *G01N 2035/00138* (2013.01); *G01N 2035/00356* (2013.01)

(56) References Cited

U.S. PATENT DOCUMENTS

| | | | |
|---|---|---|---|
| 6,495,106 | B1 | 12/2002 | Kalra et al. |
| 6,746,851 | B1 | 6/2004 | Tseung et al. |
| 7,850,912 | B2 * | 12/2010 | Favuzzi .................. G01N 1/31 422/509 |
| 8,315,899 | B2 | 11/2012 | Samuhel et al. |
| 2002/0111743 | A1 | 8/2002 | Gropp |
| 2006/0073074 | A1 | 4/2006 | Whither |
| 2006/0178776 | A1 | 8/2006 | Feingold |
| 2007/0038491 | A1 | 2/2007 | Samuhel et al. |
| 2007/0243626 | A1 | 10/2007 | Windeyer et al. |
| 2008/0113440 | A1 | 5/2008 | Gurney et al. |

FOREIGN PATENT DOCUMENTS

| | | |
|---|---|---|
| JP | 2002-181675 | 6/2002 |
| JP | 2003-519791 | 6/2003 |
| JP | 2008-516203 | 5/2008 |
| WO | 2004/074847 | 9/2004 |

OTHER PUBLICATIONS

International Preliminary Report on Patentability dated Mar. 28, 2017 in International Application No. PCT/JP2015/076755.
Extended European Search Report dated Apr. 6, 2018 in European Patent Application No. 15845267.2.

* cited by examiner

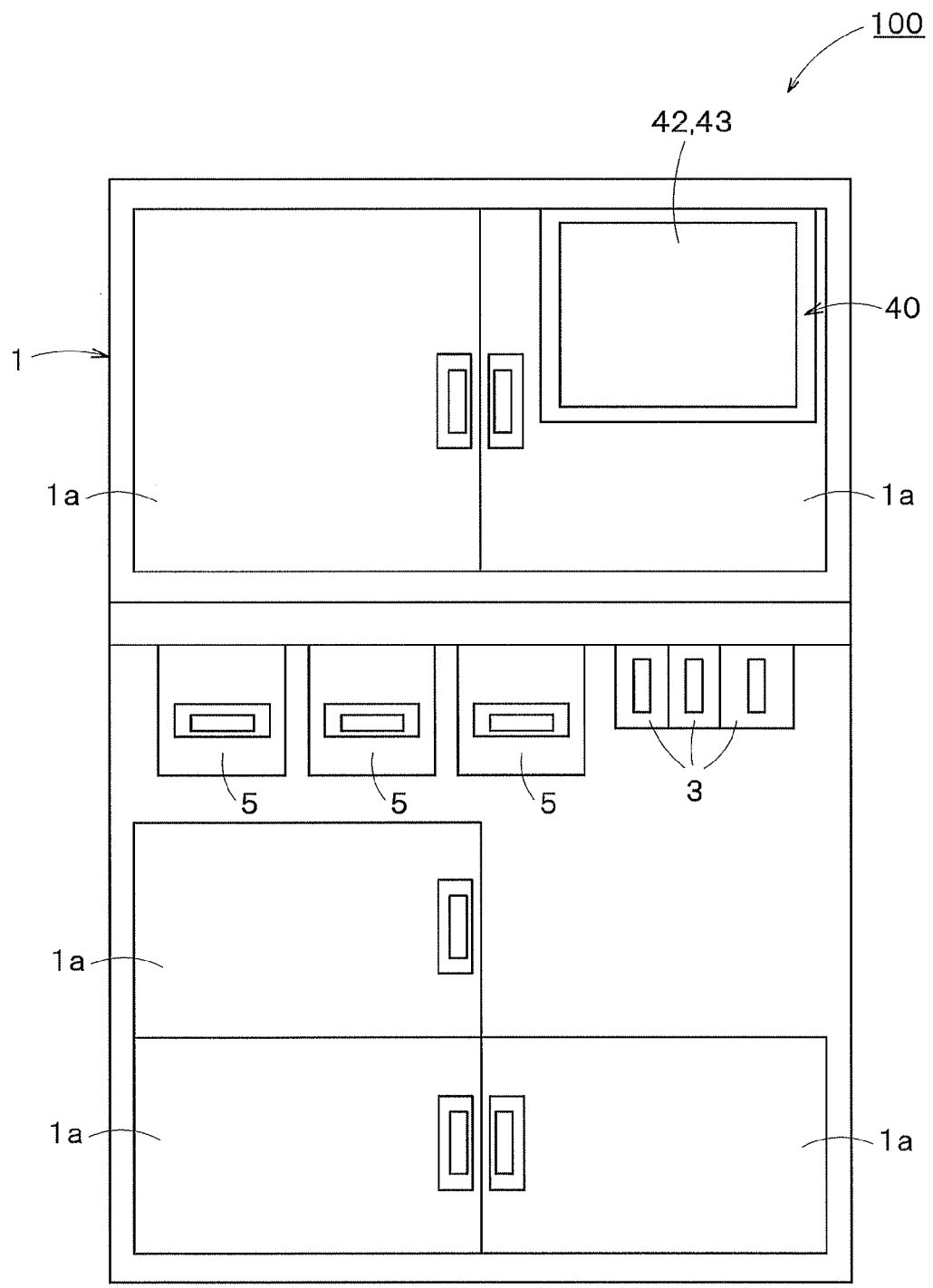
F I G. 1

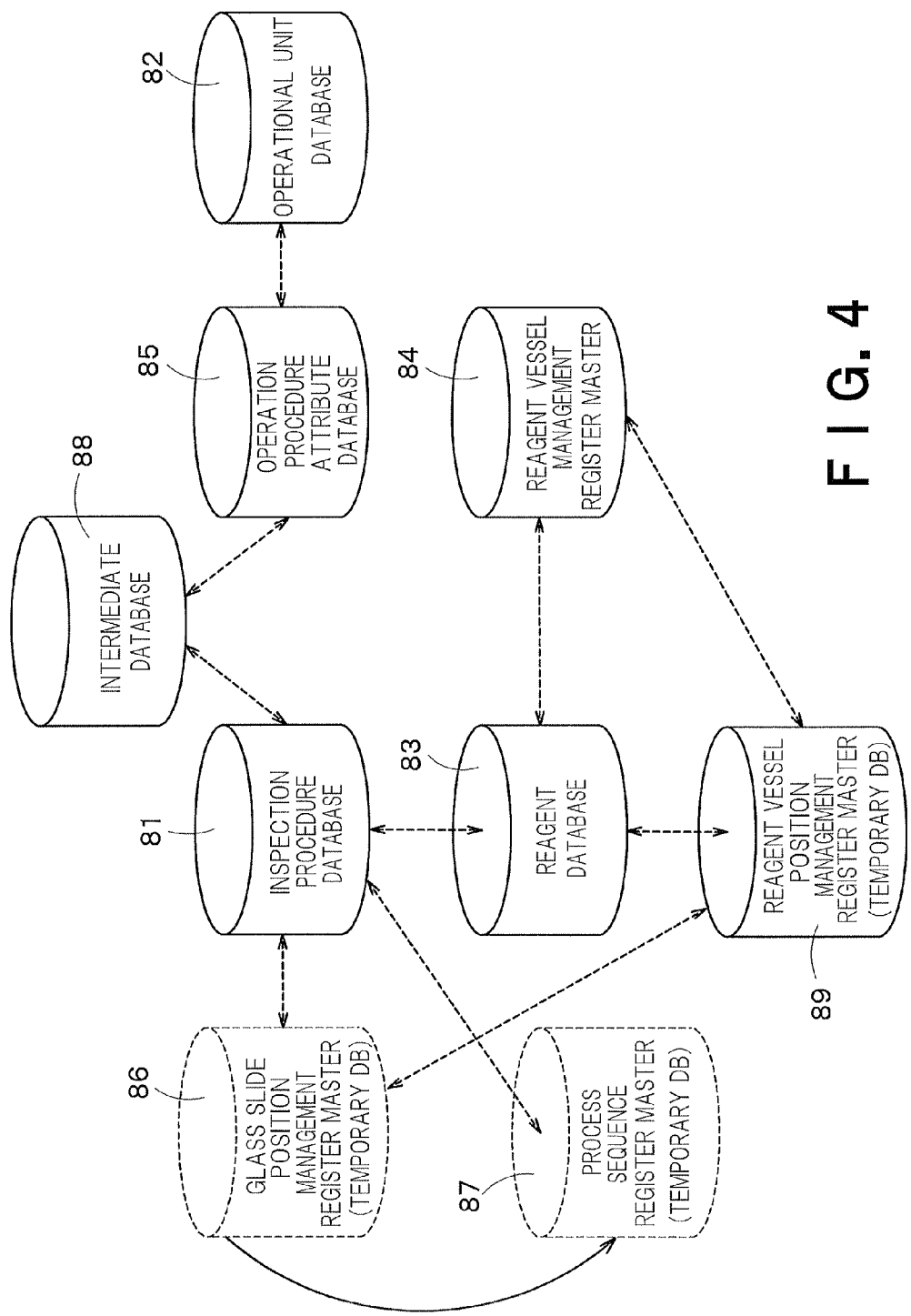
F I G. 4

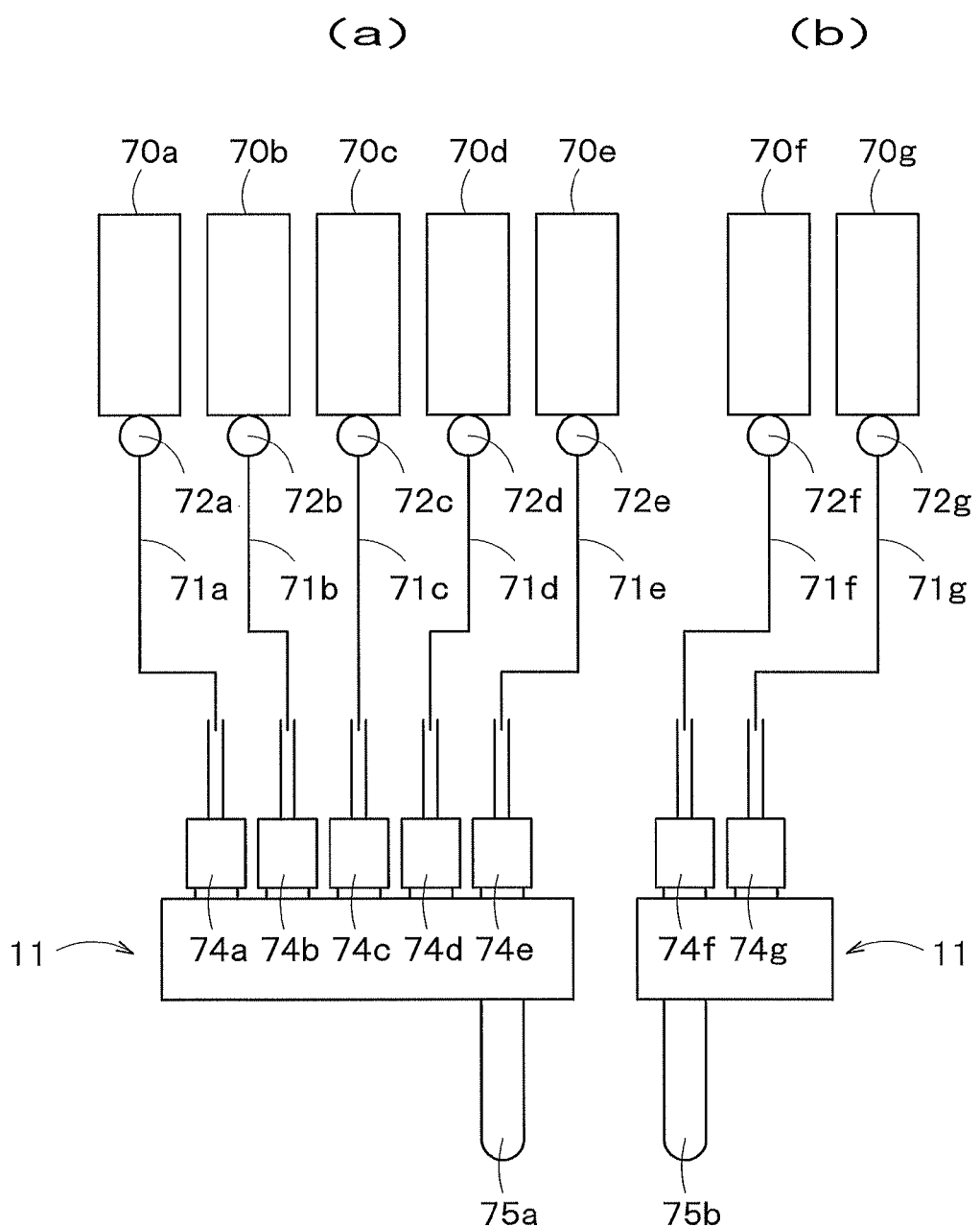
F I G. 7

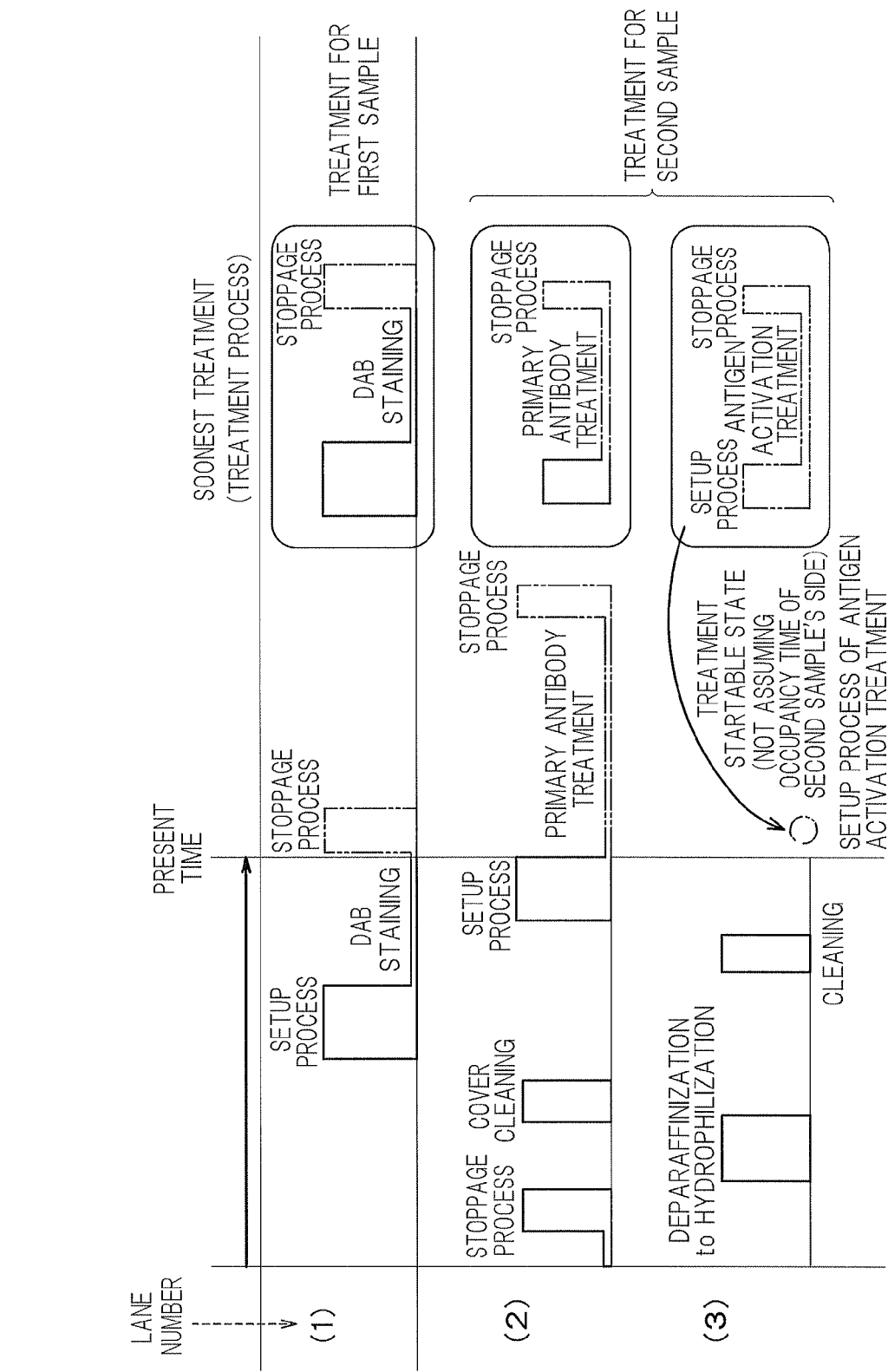
F I G. 10D

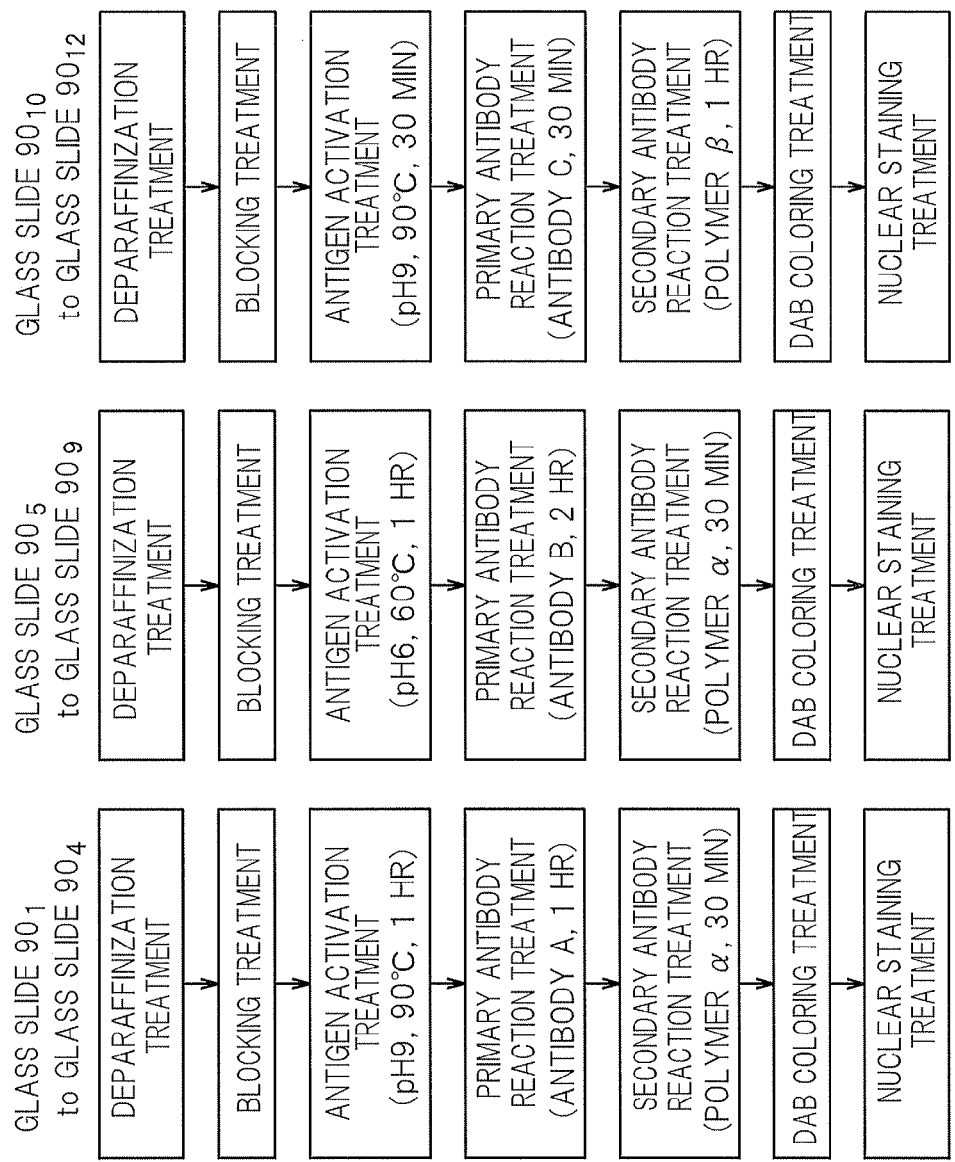
F I G. 11

AUTOMATIC TISSUE STAINING DEVICE AND AUTOMATIC TISSUE STAINING METHOD

TECHNICAL FIELD

The present invention relates to an automatic tissue staining device and an automatic tissue staining method for staining biological tissues.

BACKGROUND ART

Conventionally, there have been known automated tissue inspection devices. In this regard, U.S. Pat. No. 8,315,899 discloses a method for scheduling a device that tests biological tissues. U.S. Pat. No. 8,315,899 further discloses a method for previously generating a schedule so that times of using a robot arm do not overlap with each other when treatments are performed on slides. Specifically, in the method disclosed in U.S. Pat. No. 8,315,899, an entire schedule from the start to the end of detection treatments which are sequentially carried out is set first, and thereafter the device is operated in a mode simply according to the schedule as long as there is no addition of a new slide.

Problem to be Solved by the Invention

However, when the temperature of a sample is raised or lowered, there are cases where it takes longer than a scheduled time for the sample to reach a prescribed temperature or a time shorter than the scheduled time is enough. In this regard, in the mode disclosed in U.S. Pat. No. 8,315,899 in which the device is operated persistently according to the original schedule, the work is carried out while deviations from the planned schedule are ignored. As a result, inferiority and unevenness in reactions upon the samples often occur in the mode disclosed in U.S. Pat. No. 8,315,899.

SUMMARY OF INVENTION

The present invention, which has been made in consideration of the above-described situation, provides an automatic tissue staining device and an automatic tissue staining method which are each capable of advancing treatments according to precise treatment times without a hitch.

Solution to Problem

An automatic tissue staining device according to a first aspect of the present invention comprises:
a supply head that supplies a treatment fluid;
a horizontal direction movement unit that moves the supply head in a horizontal direction;
a holding unit that holds a plurality of glass slides on which samples are set; and
a control unit that judges occupancy status of the horizontal direction movement unit in a condition that one or more of the glass slides are situated in a first region, prior to supplying the treatment fluid from the supply head to one or more samples on the one or more glass slides situated in the first region; suspends a start of a soonest treatment for the one or more samples on the one or more glass slides situated in the first region when the horizontal direction movement unit is occupied; and permits the start of the soonest treatment for the one or more samples on the one or more glass slides situated in the first region when the horizontal direction movement unit is not occupied.

The automatic tissue staining device according to the first aspect of the present invention may further comprise:
a heating unit for heating the samples on the plurality of glass slides;
a temperature measurement unit for measuring temperature of the samples heated by the heating unit; and
an accumulation unit that judges that the temperature of the samples has reached a prescribed temperature according to result of measurement by the temperature measurement unit, starts a count, and performs accumulation, wherein:
the treatment fluid includes a treatment liquid, and
the accumulation unit stops the count when the samples on the plurality of glass slides are supplemented with the treatment liquid and restarts the count when the prescribed temperature is reached after supplementation with the treatment liquid.

The automatic tissue staining device according to the first aspect of the present invention may have a configuration where:
one or more of the glass slides are situated in a second region different from the first region,
the control unit makes a comparison between a usage schedule of the horizontal direction movement unit in a case where a treatment for one or more first samples on the one or more glass slides situated in the first region is started and a usage schedule of the horizontal direction movement unit in a treatment for one or more second samples on the one or more glass slides situated in the second region, and thereby judges whether or not there is an overlap between a time of using the horizontal direction movement unit in the case where the treatment for the one or more first samples is started and a time of using the horizontal direction movement unit in the treatment for the one or more second samples,
when there is an overlap between the time of using the horizontal direction movement unit in the case where the treatment for the one or more first samples is started and the time of using the horizontal direction movement unit in the treatment for the one or more second samples, the control unit makes a comparison between contents of a treatment schedule for the one or more first samples and contents of a treatment schedule for the one or more second samples in the overlapping time,
when the contents of the treatment schedule for the one or more first samples have priority over the contents of the treatment schedule for the one or more second samples, the control unit permits the start of the soonest treatment for the one or more first samples using the horizontal direction movement unit, and
when the contents of the treatment schedule for the one or more second samples have priority over the contents of the treatment schedule for the one or more first samples, the control unit suspends the start of the soonest treatment for the one or more first samples using the horizontal direction movement unit.

The automatic tissue staining device according to the first aspect of the present invention may have a configuration where:
one or more of the glass slides are situated in a second region different from the first region,
the control unit judges whether or not a soonest treatment for one or more second samples on the one or more glass slides situated in the second region can be started,
when the soonest treatment for the one or more second samples can be started, the control unit makes a comparison between contents of a soonest treatment schedule for one or more first samples on the one or more glass slides situated in the first region and contents of a soonest treatment schedule for the one or more second samples, when the contents of the soonest treatment schedule for the one or more first samples have priority over the contents of the soonest treatment schedule for the one or more second samples, the control unit permits the start of the soonest treatment for the one or more first samples using the horizontal direction movement unit, and when the contents of the soonest treatment schedule for the one or more second samples have priority over the contents of the soonest treatment schedule for the one or more first samples, the control unit suspends the start of the soonest treatment for the one or more first samples using the horizontal direction movement unit.

In the automatic tissue staining device according to the first aspect of the present invention, when the contents of the treatment schedule for the one or more first samples are a treatment of stopping a reaction upon the one or more first samples and the contents of the treatment schedule for the one or more second samples are a treatment other than a treatment of stopping a reaction upon the one or more second samples, the contents of the treatment schedule for the one or more first samples may be prioritized over the contents of the treatment schedule for the one or more second samples.

In the automatic tissue staining device according to the first aspect of the present invention, when the contents of the treatment schedule for the one or more first samples are a treatment other than a treatment of stopping a reaction upon the one or more first samples and the contents of the treatment schedule for the one or more second samples are a treatment other than a treatment of stopping a reaction upon the one or more second samples and a time for which the soonest treatment to be performed for the one or more first samples by using the horizontal direction movement unit has been suspended is longer than a time for which the soonest treatment to be performed for the one or more second samples by using the horizontal direction movement unit has been suspended, the contents of the treatment schedule for the one or more first samples may be prioritized over the contents of the treatment schedule for the one or more second samples.

In the automatic tissue staining device according to the first aspect of the present invention, when the contents of the treatment schedule for the one or more first samples are a treatment of stopping the reaction upon the one or more first samples and the contents of the treatment schedule for the one or more second samples are a treatment of stopping the reaction upon the one or more second samples, the contents of the treatment schedule for the one or more first samples may be prioritized over the contents of the treatment schedule for the one or more second samples if a reaction time specified for the one or more first samples being stoppage targets is shorter than a reaction time specified for the one or more second samples being stoppage targets.

In the automatic tissue staining device according to the first aspect of the present invention, when the one or more first samples and the one or more second samples are samples for which an immunostaining method has been specified as a staining method and the contents of the treatment schedule for the one or more first samples are a treatment of stopping the reaction upon the one or more first samples and the contents of the treatment schedule for the one or more second samples are a treatment of stopping the reaction upon the one or more second samples, the contents of the treatment schedule for the one or more first samples may be prioritized over the contents of the treatment schedule for the one or more second samples if the contents of the treatment schedule for the one or more first samples are a treatment of stopping a reaction of a primary antibody upon an antigen in the one or more first samples and the contents of the treatment schedule for the one or more second samples are a treatment other than a treatment of stopping a reaction of a primary antibody upon an antigen in the one or more second samples.

In the automatic tissue staining device according to the first aspect of the present invention, when the treatment for the one or more second samples cannot be started and there is no overlap between a time of using the horizontal direction movement unit in the treatment schedule for the one or more first samples and a time of using the horizontal direction movement unit in the treatment schedule for the one or more second samples, the control unit may permit the treatment for the one or more first samples.

The automatic tissue staining device according to the first aspect of the present invention may further comprise a plurality of lanes, wherein:

the same number of holding units as lanes is provided,
the lanes are provided respectively with the holding units,
a certain one of the lanes corresponds to the first region, and
another lane different from the lane corresponding to the first region corresponds to the second region.

The automatic tissue staining device according to the first aspect of the present invention may have a configuration where the control unit compares treatment schedules from a present time in integrated process sequences which are generated for a plurality of regions respectively to each include a sequence of treatment processes for a plurality of samples in each of the plurality of regions with each other, thereby makes a comparison between a usage schedule of the horizontal direction movement unit in a case where a treatment for a plurality of first samples situated in a certain region in the plurality of regions is started and a usage schedule of the horizontal direction movement unit in a treatment for a plurality of second samples situated in another region, and thereby judges whether or not there is an overlap between the time of using the horizontal direction movement unit in the case where the treatment for the plurality of first samples is started and the time of using the horizontal direction movement unit in the treatment for the plurality of second samples.

In the automatic tissue staining device according to the first aspect of the present invention, the integrated process sequences may be generated by comparing individual process sequences, each including a plurality of treatment processes performed for the plurality of samples respectively, with each other in each of the plurality of regions so as to consecutively perform treatment processes of the same contents on a plurality of samples on each of the plurality of regions.

In the automatic tissue staining device according to the first aspect of the present invention, the integrated process sequences may be generated by comparing contents of treatment liquids included in the treatment fluids supplied to the respective samples in the consecutively performed treatment processes of the same contents so that samples using the same treatment liquid are consecutively supplied with the treatment liquid.

In the automatic tissue staining device according to the first aspect of the present invention, the integrated process sequences may be generated so as to supply the treatment liquid included in the treatment fluid to a sample whose reaction time is long prior to a sample whose reaction time is short in the consecutively performed treatment processes of the same contents.

The automatic tissue staining device according to the first aspect of the present invention may further comprise:
a heating unit for heating the samples on the plurality of glass slides; and
a temperature measurement unit for measuring temperature of the samples heated by the heating unit,
wherein the integrated process sequences are generated so as to supply a treatment liquid included in the treatment fluid to a sample whose reaction temperature is high prior to a sample whose reaction temperature is low in the consecutively performed treatment processes of the same contents.

An automatic tissue staining device according to a second aspect of the present invention comprises:
a supply head that supplies a treatment fluid;
a holding unit that holds a plurality of glass slides on which samples are set;
a control unit that compares attributes of inspection methods performed respectively for the samples on the plurality of glass slides with each other, thereby judges whether or not the inspection methods performed for the samples belong to the same attribute, and specifies one or more glass slides that should be removed from the holding unit so that inspection methods of the same attribute are performed for the samples on the glass slides held in the holding unit when the attribute of the inspection method performed for a certain sample and the attribute of the inspection method performed for another sample differ from each other; and
a notification unit that notifies of the one or more glass slides specified by the control unit to be removed.

The automatic tissue staining device according to the second aspect of the present invention may further comprise a plurality of lanes, wherein:
the same number of holding units as lanes is provided,
the lanes are provided respectively with the holding units, and
the control unit specifies one or more glass slides that should be removed from the holding unit so that inspection methods of the same attribute are performed for the samples on all the glass slides held in the holding unit of a certain one of the lanes.

In the automatic tissue staining device according to the second aspect of the present invention, the notification unit may notify of another lane on which the one or more glass slides specified to be removed should be set.

An automatic tissue staining device according to a third aspect of the present invention comprises:
a supply head that supplies a treatment fluid;
a holding unit that holds a plurality of glass slides on which samples are set; and
a control unit that executes control so as to consecutively perform treatment processes of the same contents for a plurality of samples by comparing individual process sequences, each including a plurality of treatment processes performed for each of the samples, with each other.

The automatic tissue staining device according to the third aspect of the present invention may further comprise a horizontal direction movement unit that moves the supply head in a horizontal direction, wherein:
one or more of the glass slides are situated in a first region,
one or more of the glass slides are situated in a second region different from the first region,
the control unit makes a comparison between a usage schedule of the horizontal direction movement unit in a treatment for one or more first samples on the one or more glass slides situated in the first region and a usage schedule of the horizontal direction movement unit in a treatment for one or more second samples on the one or more glass slides situated in the second region and thereby judges whether or not there is an overlap between a time of using the horizontal direction movement unit in the treatment for the one or more first samples and a time of using the horizontal direction movement unit in the treatment for the one or more second samples,
when there is an overlap between the time of using the horizontal direction movement unit in the treatment for the one or more first samples and the time of using the horizontal direction movement unit in the treatment for the one or more second samples, the control unit makes a comparison between contents of a treatment schedule for the one or more first samples and contents of a treatment schedule for the one or more second samples in the overlapping time,
when the contents of the treatment schedule for the one or more first samples have priority over the contents of the treatment schedule for the one or more second samples, the control unit permits a start of a soonest treatment for the one or more first samples using the horizontal direction movement unit, and
when the contents of the treatment schedule for the one or more second samples have priority over the contents of the treatment schedule for the one or more first samples, the control unit suspends the start of the soonest treatment for the one or more first samples using the horizontal direction movement unit.

The automatic tissue staining device according to the third aspect of the present invention may further comprise a horizontal direction movement unit that moves the supply head in a horizontal direction, wherein:
one or more of the glass slides are situated in a first region,
one or more of the glass slides are situated in a second region different from the first region,
the control unit judges whether or not a soonest treatment for one or more second samples on the one or more glass slides situated in the second region can be started,
when the soonest treatment for the one or more second samples can be started, the control unit makes a comparison between contents of a treatment schedule for one or more first samples on the one or more glass slides situated in the first region and contents of a treatment schedule for the one or more second samples,
when the contents of the treatment schedule for the one or more first samples have priority over the contents of the treatment schedule for the one or more second samples, the control unit permits a start of a soonest treatment for the one or more first samples using the horizontal direction movement unit, and
when the contents of the treatment schedule for the one or more second samples have priority over the contents of the treatment schedule for the one or more first samples, the control unit suspends the start of the soonest treatment for the one or more first samples using the horizontal direction movement unit.

An automatic tissue staining device according to a fourth aspect of the present invention comprises:
a supply head that supplies a treatment liquid;
a holding unit that holds a plurality of glass slides on which samples are set;
a plurality of reservoir units that reserve the treatment liquid;

a plurality of guide pipes provided corresponding to the plurality of reservoir units respectively to guide the treatment liquid supplied from the plurality of reservoir units; and liquid sending units that send out the treatment liquid from the plurality of reservoir units into the plurality of guide pipes, wherein the supply head includes:

a nozzle that discharges the treatment liquid guided by each of the guide pipes onto a sample on each of the plurality of glass slides; and a plurality of check valves provided between respective discharge-side ends of the plurality of guide pipes and the nozzle to prevent a backward flow of the treatment fluid into the plurality of guide pipes.

An automatic tissue staining method according to a fifth aspect of the present invention is an automatic tissue staining method using an automatic tissue staining device equipped with a supply head that supplies a treatment fluid, a horizontal direction movement unit that moves the supply head in a horizontal direction, and a holding unit that holds a plurality of glass slides on which samples are set, and the automatic tissue staining method comprises the steps of:

judging occupancy status of the horizontal direction movement unit in a condition that one or more of the glass slides are situated in a first region, prior to supplying the treatment fluid from the supply head to one or more samples on the one or more glass slides situated in the first region;

suspending a start of a soonest treatment for the one or more samples on the one or more glass slides situated in the first region when the horizontal direction movement unit is occupied; and permitting the start of the soonest treatment for the one or more samples on the one or more glass slides situated in the first region when the horizontal direction movement unit is not occupied.

Advantageous Effects of Invention

According to the present invention, the occupancy status of the horizontal direction movement unit is judged prior to supplying the treatment fluid from the supply head to the samples on the glass slides situated in the first region for which a treatment is going to be performed. When the horizontal direction movement unit is occupied, the start of the treatment for the samples on the glass slides situated in the first region is suspended. When the horizontal direction movement unit is not occupied, the treatment for the samples on the glass slides situated in the first region is permitted. Thus, according to the present invention, treatments can be carried out mostly according to precise treatment times while grasping the usage status of the horizontal direction movement unit in real time.

BRIEF DESCRIPTION OF DRAWINGS

FIG. 1 is a schematic front view showing an automatic tissue staining device according to an embodiment of the present invention as viewed from the front.

FIG. 4 is a schematic diagram showing databases and the like in the automatic tissue staining device according to the embodiment of the present invention.

FIG. 7 is a schematic diagram showing reservoir units, check valves, etc. of the automatic tissue staining device according to the embodiment of the present invention.

FIG. 10D is a diagram corresponding to FIG. 10A, FIG. 10D showing usage schedules when a prescribed time has passed since the time point shown in FIG. 10C.

FIG. 11 is a diagram for explaining a mode of generating the integrated process sequence in the automatic tissue staining device according to the embodiment of the present invention.

DESCRIPTION OF EMBODIMENTS

Embodiments
<<Configuration>>

An embodiment of an automatic tissue staining device and an automatic tissue staining method according to the present invention will be described below with reference to drawings. FIGS. 1 to 13 are diagrams for explaining the embodiment of the present invention.

Figure 2:
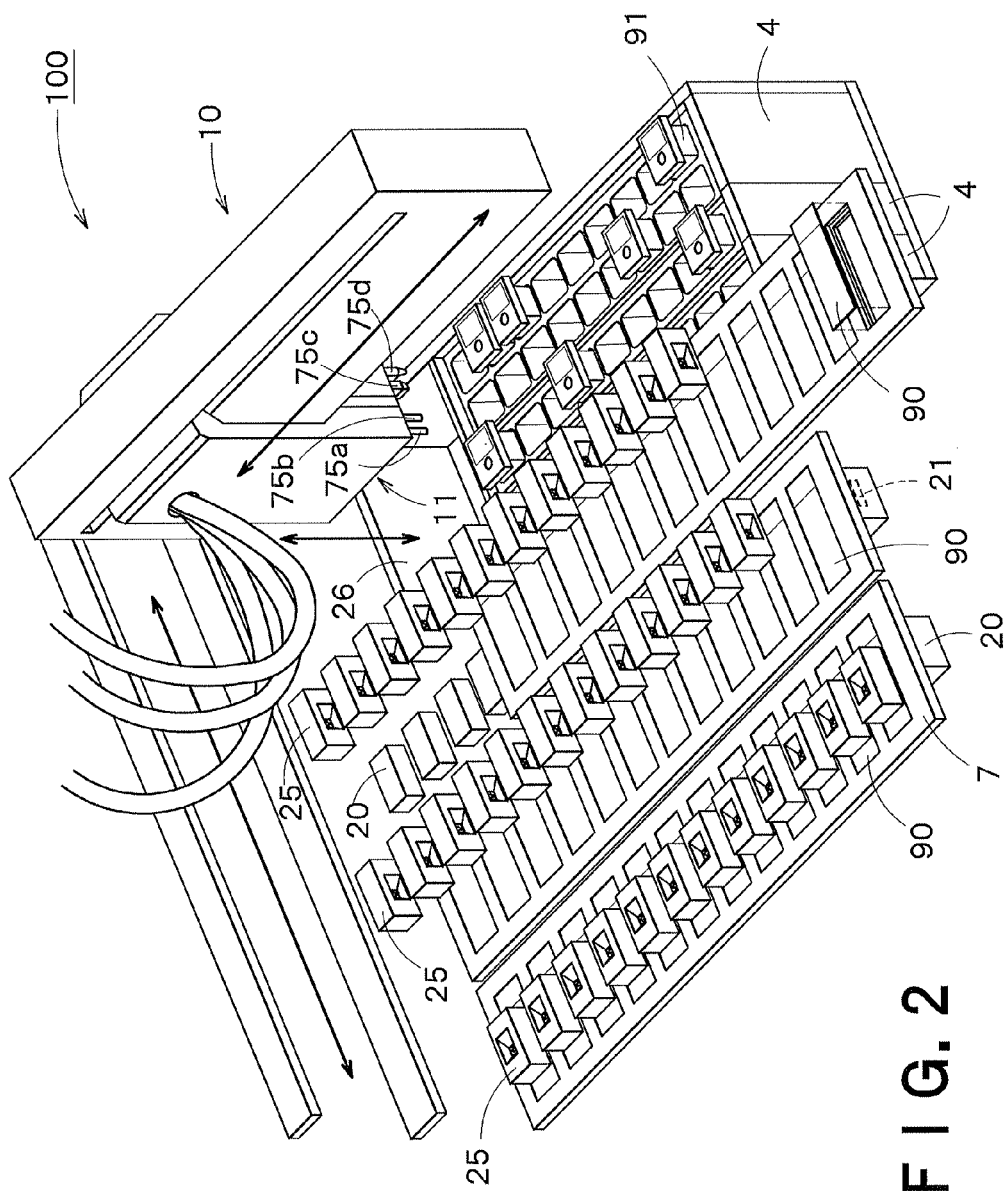
FIG. 2 is a perspective view showing a supply head, a horizontal direction movement unit, heating units, covers and so forth stored in a housing of the automatic tissue staining device according to the embodiment of the present invention.
Figure 5:
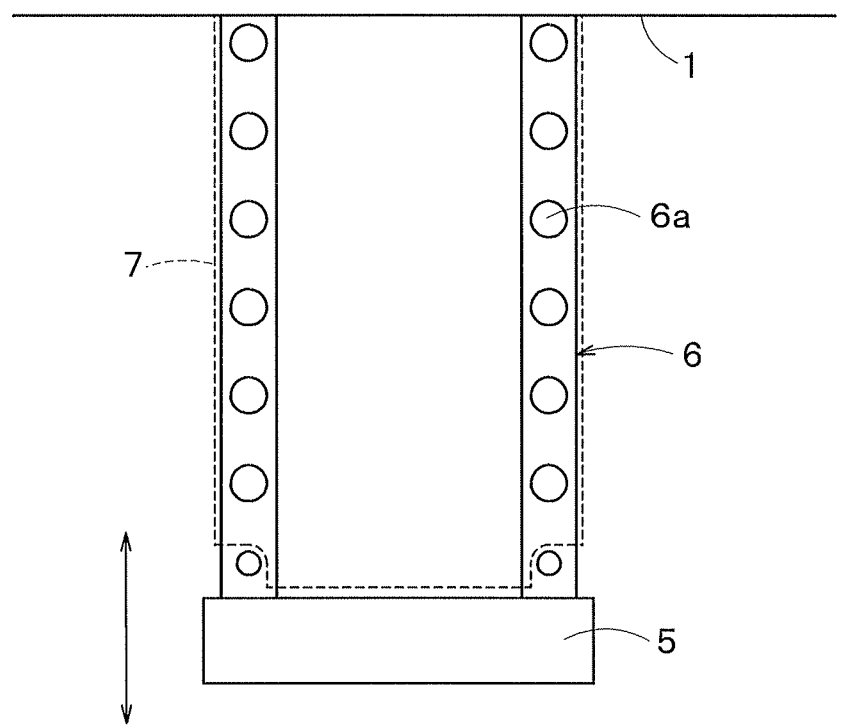
FIG. 5 is a schematic top view showing a lane, elastic members, etc. of the automatic tissue staining device according to the embodiment of the present invention.

As shown in FIG. 1, an automatic tissue staining device 100 according to this embodiment includes a housing 1 having a plurality of opening/closing doors 1a, and a plurality of (three in this embodiment) drawers 5 that can be freely pulled out forward with respect to the housing 1. In the opening/closing doors 1a of an upper stage of the aforementioned housing 1, a supply head 11 for supplying treatment fluids and a horizontal direction movement unit 10, such as a Cartesian coordinate robot, for moving the supply head 11 in a horizontal direction in the housing 1 are installed as shown in FIG. 2. As shown in FIG. 5, each of the aforementioned drawers 5 is equipped with a lane 6, and each lane 6 is equipped with a holding unit 7 including a tray or the like. Specifically, the same number of holding units 7 as the lanes 6 are provided, and the holding units 7 are provided for the lanes 6 respectively. Each lane 6 has a plurality of elastic members 6a, such as springs, for applying elastic force to the holding unit 7 set on the lane 6 from below. In this embodiment, three lanes 6 and three holding units 7 are arranged. As shown in FIG. 2, each holding unit 7 is configured to be able to hold a plurality of (twelve in this embodiment) glass slides 90 on each of which a sample has been set.

As shown in FIG. 2, the automatic tissue staining device 100 includes: heating units 20 each for heating a glass slide 90 and thereby heating the sample on the glass slide 90, and temperature measurement units 21 each for measuring the temperature of the sample heated by a heating unit 20. In this embodiment, each temperature measurement unit 21, such as a temperature sensor, is embedded in a heating unit 20 so that the temperature of the sample on the glass slide 90 is indirectly measured by measuring temperature with the temperature measurement unit 21.

In the opening/closing doors 1a of a middle stage and a lower stage of the housing 1 shown in FIG. 1, reservoir units 70a to 70g (explained later) for reserving treatment liquids and a liquid waste unit (not illustrated) for storing liquid waste are arranged.

Incidentally, the "treatment fluid" in this embodiment can mean not only a treatment liquid but also a treatment gas. The "sample" in this embodiment mainly means a thin section of a biological tissue, cultured cells or the like adhering to a glass slide 90. The description of this embodiment will be given of a case where there exists a sample for which a publicly known immunostaining method, staining only parts of the sample's surface where a specified antigen exists, has been specified as the staining method. In the immunostaining method, tissue embedded in a material such as paraffin is sliced by using a microtome or the like and a sample is prepared by affixing such a tissue slice having an exposed tissue cross section on a glass slide. In this embodiment, a "primary antibody" means an antibody (or a detection reagent containing the antibody) supposed to bind to the aforementioned specified antigen, and a "secondary antibody" means a reagent containing a polymer labeled with an antibody supposed to bind to the primary antibody, an enzyme, etc. Parts of the sample's surface where the antigen has not appeared do not bind with a primary antibody or a secondary antibody. Thus, even if a chromogenic reaction such the DAB (diaminobenzidine) reaction is performed on an enzyme or the like that has labeled the secondary antibody, the reaction results in no staining. This also makes it possible to judge a sample not containing the antigen as negative. Incidentally, the "sample" in the present application can mean not only a thin section of a biological tissue, cultured cells or the like mentioned above but also a thin section of a biological tissue, cultured cells or the like already bound with an antibody such as "a primary antibody" or "a primary antibody and a secondary antibody."

As shown in FIG. 2, the automatic tissue staining device 100 further includes reagent vessel stands 4 capable of holding a plurality of reagent vessels 91 storing reagents in the housing 1. In this embodiment, three reagent vessel stands 4 are provided. The respective reagent vessel stands 4 are set on three drawers 3 (see FIG. 1) that can be freely pulled out forward with respect to the housing 1.

Figure 3:
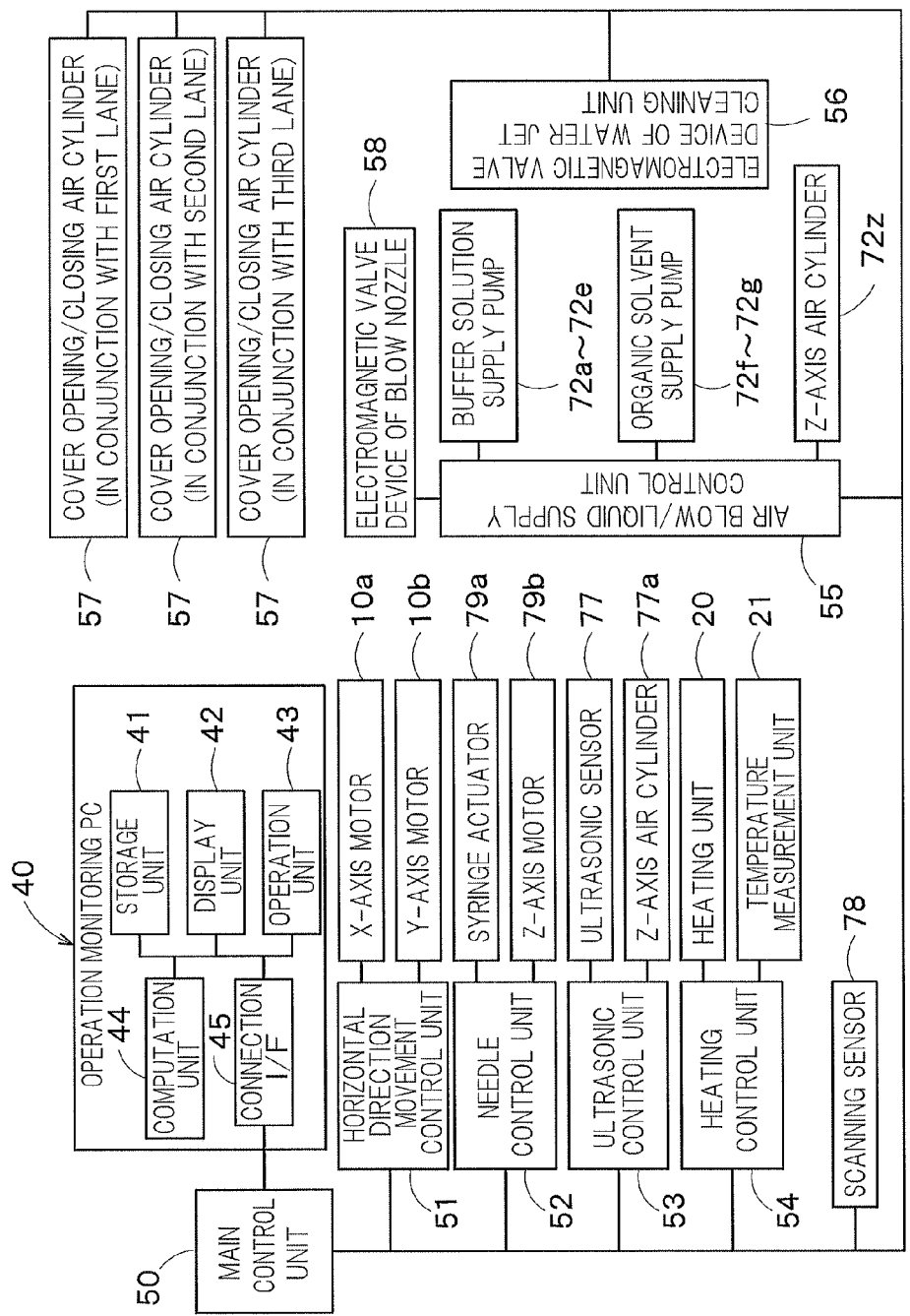
FIG. 3 is a block diagram showing the connection configuration of the automatic tissue staining device according to the embodiment of the present invention.

Further, as shown in FIG. 1, an operation monitoring device 40 is provided on a front exterior surface of the housing 1. As shown in FIG. 3, the operation monitoring device 40 includes a storage unit 41 for storing a variety of information, a display unit 42 for displaying a variety of information, an operation unit 43 for receiving operation inputs from an operator, and a computation unit 44 for performing computation processes. In cases where the operation monitoring device 40 is a touch panel, the display unit 42 and the operation unit 43 are implemented by one touch panel. The operation monitoring device 40 is connected via a connection interface 45 to a main control unit 50 that controls the whole of the automatic tissue staining device 100. The main control unit 50 is connected to a horizontal direction movement control unit 51, a needle control unit 52, an ultrasonic control unit 53, a heating control unit 54, a scanning sensor 78, an air blow/liquid supply control unit 55, an electromagnetic valve device 56 of a water jet cleaning unit 26, a cover opening/closing air cylinder 57, etc., which will be explained later, so as to control these components.

The storage unit 41 stores an inspection procedure database 81, an operational unit database 82, a reagent database 83, a reagent vessel management register master 84, an operation procedure attribute database 85 and an intermediate database 88 shown in FIG. 4. In the inspection procedure database 81, each inspection method and its operation procedure are registered while associating them with an "inspection method code." In the operational unit database 82, each operational unit for forming the operation procedure and the contents of each operational unit are recorded. In the reagent database 83, each reagent to be specified for each operational unit is registered while associating each reagent with a "reagent code." In the reagent vessel management register master 84, a "reagent vessel code" and the stored reagent code are registered while associating them with each other. The amount of storage, a date, etc. are also recorded (for the purpose of abnormality detection or the like) in the reagent vessel management register master 84. In the operation procedure attribute database 85, "attributes" of the operation procedures are recorded. The intermediate database 88 is connected to each of the inspection procedure database 81 and the operation procedure attribute database 85. The storage unit 41 further stores a glass slide position management register master 86, a process sequence register master 87 and a reagent vessel position management register master 89. The glass slide position management register master 86 stores temporary information such as an inspection code of the inspection method performed on each glass slide 90 held in a holding unit 7 in regard to each position of each slide glass 90 in the lane 6. The process sequence register master 87 stores a sequence of treatments to be performed in each lane 6 (integrated process sequence which will be explained later) generated based on the inspection methods of the samples in each lane 6. The reagent vessel position management register master 89 stores the reagent vessel code of each reagent vessel 91 held on a reagent vessel stand 4 in regard to each position of each reagent vessel 91 in the drawer 3.

The operational unit database 82 communicates information with the operation procedure attribute database 85. The inspection procedure database 81 communicates information with the operation procedure attribute database 85 via the intermediate database 88 while also communicating information with the reagent database 83. The glass slide position management register master 86 communicates information with the inspection procedure database 81 and the reagent vessel position management register master 89. The process sequence register master 87 communicates information with the inspection procedure database 81. The reagent database 83 communicates information also with the reagent vessel management register master 84. The glass slide position management register master 86 communicates information also with the process sequence register master 87. Incidentally, an unshown bar code reader is connected to the operation monitoring device 40. By scanning a two-dimensional bar code or the like affixed on a reagent vessel 91 by using the bar code reader, information such as the reagent vessel code of the reagent vessel 91 and the reagent code of the reagent stored in the reagent vessel 91 can be registered in the reagent vessel management register master 84. Also for a new reagent that has not been registered in the reagent database 83 yet, the reagent code of the new reagent and other information on the reagent can be registered in the reagent database 83 by scanning a two-dimensional bar code corresponding to the new reagent.

As shown in FIG. 3, the horizontal direction movement unit 10 includes an X-axis motor 10a for moving the supply head 11 in a width direction of the housing 1 (horizontal direction in FIG. 1), a Y-axis motor 10b for moving the supply head 11 in a depth direction of the housing 1 (direction of the normal to the sheet of FIG. 1), and the horizontal direction movement control unit 51 for controlling the X-axis motor 10a and the Y-axis motor 10b. The automatic tissue staining device 100 of this embodiment further includes the heating control unit 54 for controlling each heating unit 20 based on measurement results inputted from each temperature measurement unit 21.

The automatic tissue staining device 100 of this embodiment includes a supply unit for supplying the treatment fluids. As shown in the (a) part of FIG. 7 and the (b) part of FIG. 7, the supply unit includes a plurality of (seven in this embodiment) reservoir units 70a to 70g for reserving treatment fluids, guide pipes 71a to 71g provided respectively corresponding to the reservoir units 70a to 70g to guide the treatment fluids supplied from the respective reservoir units 70a to 70g, liquid sending units 72a to 72g for sending out the treatment fluids from the reservoir units 70a to 70g into the guide pipes 71a to 71g, the supply head 11 having liquid supply nozzles 75a and 75b for discharging the treatment fluids guided by the guide pipes 71a to 71g to samples on glass slides 90, and check valves 74a to 74g provided between discharge-side ends of the guide pipes 71a to 71g and the liquid supply nozzles 75a and 75b to prevent the backward flow of the treatment fluids into the guide pipes 71a to 71g.

The aforementioned reservoir units 70a to 70g include a plurality of (two in this embodiment) organic solvent reservoir units 70f and 70g storing organic solvents (see (b) of FIG. 7) and a plurality of (five in this embodiment) buffer solution reservoir units 70a to 70e storing buffer solutions (see (a) of FIG. 7). The organic solvent reservoir units 70f and 70g reserve organic solvents different from each other. Similarly, the buffer solution reservoir units 70a to 70e reserve buffer solutions different from each other. The aforementioned liquid sending units 72a to 72g include buffer solution supply pumps 72a to 72e for sending out the buffer solutions from the buffer solution reservoir units 70a to 70e and organic solvent supply pumps 72f and 72g for sending out the organic solvents from the organic solvent reservoir units 70f and 70g (see FIG. 3). For example, one of the organic solvents is alcohol such as ethanol. While this embodiment is described on the assumption that buffer solutions are mainly used, for example, this embodiment is not limited to such examples; it is also possible to use water such as pure water instead of the buffer solutions. In such cases where water is used, water is stored in one or more of the plurality of buffer solution reservoir units 70a to 70e.

Figure 6:
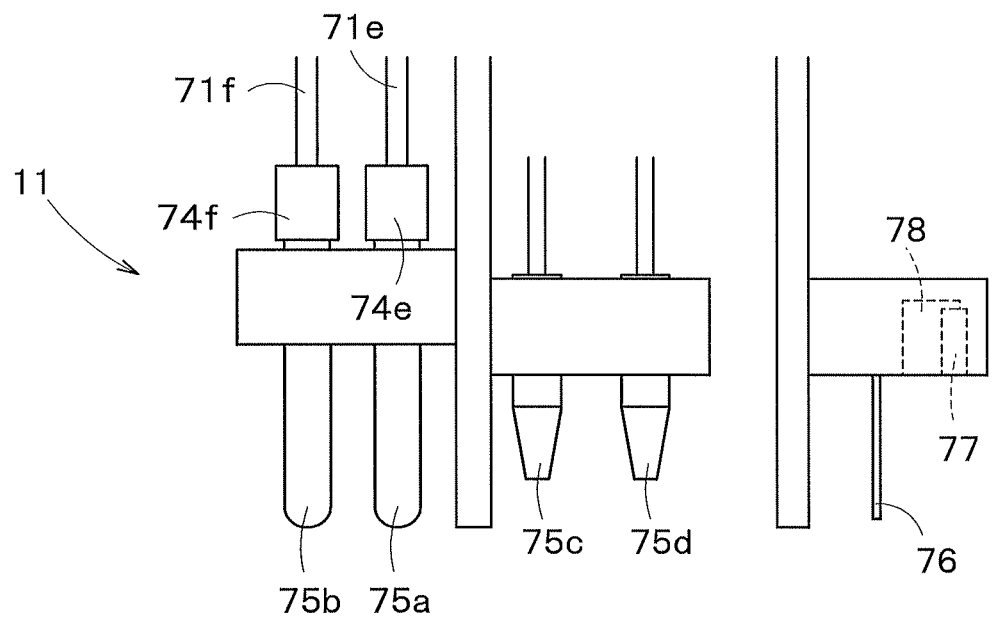
FIG. 6 is a schematic front view showing the supply head of the automatic tissue staining device according to the embodiment of the present invention.

As shown in FIG. 6, the aforementioned liquid supply nozzles 75a and 75b include an organic solvent nozzle 75b for supplying an organic solvent to samples on glass slides 90 and a buffer solution nozzle 75a for supplying a buffer solution or water to samples on glass slides 90. The supply head 11 includes not only such liquid supply nozzles 75a and 75b but also blow nozzles 75c and 75d for supplying gas to samples on glass slides 90. The nozzles 75a to 75d are constituted of the liquid supply nozzles 75a and 75b and the blow nozzles 75c and 75d

Incidentally, (a) of FIG. 7 is a diagram showing the reservoir units 70a to 70e, the guide pipes 71a to 71e, the liquid sending units 72a to 72e and the check valves 74a to 74e corresponding to the buffer solution nozzle 75a in FIG. 6, while (b) of FIG. 7 is a diagram showing the reservoir units 70f and 70g, the guide pipes 71f and 71g, the liquid sending units 72f and 72g and the check valves 74f and 74g corresponding to the organic solvent nozzle 75b in FIG. 6.

The blow nozzles 75c and 75d shown in FIG. 6 include a first blow nozzle 75c having a discharge port in a slit shape extending in the depth direction of the housing and a second blow nozzle 75d having a discharge port in a substantially circular shape. As shown in FIG. 3, a Z-axis air cylinder 72z is connected to the organic solvent nozzle 75b and the buffer solution nozzle 75a to move these nozzles in the vertical direction. Further, the air blow/liquid supply control unit 55 is connected to the buffer solution supply pumps 72a to 72e, the organic solvent supply pumps 72f and 72g and the Z-axis air cylinder 72z explained above so as to control these components. The air blow/liquid supply control unit 55 is connected also to an electromagnetic valve device 58 of the blow nozzles 75c and 75d so as to also control the electromagnetic valve device 58 of the blow nozzles 75c and 75d.

Incidentally, when different treatment liquids are discharged by using the same liquid supply nozzle 75a or 75b (i.e., the buffer solution nozzle 75a or the organic solvent nozzle 75b), the liquid to be discharge is switched at the deepest position in the lane 6 and thereafter the discharge is performed for a while (the so-called "preliminary discharge" is performed), by which discharge of an incorrect treatment liquid onto the sample or the like is prevented and contamination is avoided. However, in cases where a treatment liquid to be discharged onto one or more sample on one or more glass slide 90 situated on a lane 6 to be treated from now ("first sample" which will be explained later) is the same as a treatment liquid that has been discharged onto one or more sample on one or more glass slide 90 situated on another lane 6 ("second sample" which will be explained later), for example, the air blow/liquid supply control unit 55 may execute the control so as not to perform the preliminary discharge from the liquid supply nozzle 75a or 75b.

As shown in FIG. 6, the supply head 11 includes not only the aforementioned nozzles 75a to 75d but also a reagent needle 76 for sucking in a reagent from a reagent vessel 91 and dropping the reagent onto a sample on a glass slide 90, a scanning sensor 78 for scanning identification information affixed on a reagent vessel 91 and identification information such as a two-dimensional bar code affixed on a glass slide 90, and an ultrasonic sensor 77 for measuring distance in the vertical direction.

As shown in FIG. 3, a needle control unit 52 for controlling the movement of the reagent needle 76 is provided in this embodiment. The needle control unit 52 is connected to a syringe actuator 79a for driving a syringe (not shown) connected to the reagent needle 76 and to a Z-axis motor 79b for moving the reagent needle 76 in the vertical direction. The needle control unit 52 controls the syringe actuator 79a and the Z-axis motor 79b. The automatic tissue staining device 100 of this embodiment further includes a Z-axis air cylinder 77a for moving the aforementioned ultrasonic sensor 77 in the vertical direction and an ultrasonic control unit 53 for controlling the ultrasonic sensor 77.

As shown in FIG. 2, the automatic tissue staining device 100 of this embodiment further includes a water jet cleaning unit 26 for cleaning the reagent needle 76. The water jet cleaning unit 26 is situated at an initial position to which the horizontal direction movement unit 10 returns when the horizontal direction movement unit 10 is not driven. The water jet cleaning unit 26 is configured so that the reagent needle 76 can be cleaned by a cleaning liquid discharged like a water jet. The cleaning of the reagent needle 76 is carried out by having the reagent needle 76 suck in a prescribed amount of the cleaning liquid until the cleaning liquid reaches the inside of the syringe (not shown) connected to the reagent needle 76 and thereafter having the reagent needle 76 discharge the cleaning liquid. The suction and discharge of the cleaning liquid are repeated multiple times. As shown in FIG. 3, the water jet cleaning unit 26 further includes an electromagnetic valve device 56 to be used for discharging the cleaning liquid like a water jet.

As shown in FIG. 2, in this embodiment, a plurality of (thirty-six in this embodiment) covers 25, each capable of covering a part of a glass slide 90, are provided corresponding to the glass slides 90 respectively. Each cover 25 covers a part of a glass slide 90 in an antigen retrieval process (excluding cases where an enzyme is used), a primary antibody reaction and a secondary antibody reaction which will be explained later. In this embodiment, twelve glass slides 90 are held on each lane 6 and twelve covers 25 and twelve heating units 20 are provided corresponding to the twelve glass slides 90, for example. The twelve covers 25 arranged in each lane 6 are provided with a cover opening/closing air cylinder 57 (see FIG. 3) for integrally opening and closing these covers 25. The automatic tissue staining device 100 of this embodiment is equipped with three cover opening/closing air cylinders 57 in total. In FIG. 3, the cover opening/closing air cylinders 57 corresponding to the respective lanes 6 are indicated with a description "IN CONJUNCTION WITH FIRST LANE," "IN CONJUNCTION WITH SECOND LANE" or "IN CONJUNCTION WITH THIRD LANE."

In this embodiment, a glass slide 90 situated on a lane 6 on which a treatment of supplying a treatment fluid from the supply head 11 is to be performed from now will be referred to as a "glass slide situated in the first region," and a glass slide 90 situated on a lane 6 other than the aforementioned lane 6 will be referred to as a "glass slide situated in the second region." More specifically, when a treatment fluid is going to be supplied from the supply head 11 to a glass slide 90 situated on the rightmost lane 6 in FIG. 2 from now, the glass slides 90 situated on the rightmost lane 6 in FIG. 2 are glass slides 90 situated in the first region, and the glass slides 90 situated on the other lanes 6, that is, the leftmost lane 6 and the center lane 6 in FIG. 2, are glass slides 90 situated in the second region. Further, in this embodiment, a sample on a "glass slide situated in the first region" will be referred to as a "first sample," and a sample on a "glass slide situated in the second region" will be referred to as a "second sample." Specifically, suppose that a treatment fluid is going to be supplied from the supply head 11 to a glass slide 90 situated on the rightmost lane 6 in FIG. 2 from now, the samples on the glass slides 90 situated on the rightmost lane 6 in FIG. 2 are first samples, and the samples on the glass slides 90 situated on the other lanes 6, that is, the leftmost lane 6 and the center lane 6 in FIG. 2, are second samples.

Incidentally, a simple term "control unit" in this embodiment collectively means the main control unit 50, the horizontal direction movement control unit 51, the needle control unit 52, the ultrasonic control unit 53, the heating control unit 54 and the air blow/liquid supply control unit 55 which have been explained above. The "control unit" includes all components controlling the automatic tissue staining device 100. The following explanation will be given by using this term "control unit."

The control unit 50 to 55 (e.g., the main control unit 50) in this embodiment judges the occupancy status of the horizontal direction movement unit 10 prior to supplying a treatment fluid from the supply head 11 to first samples on glass slides 90 situated in the first region. If the horizontal direction movement unit 10 is occupied, the start of the soonest treatment for the first samples on the glass slides 90 situated in the first region is suspended. If the horizontal direction movement unit 10 is not occupied, the start of the soonest treatment for the first samples on a glass slides 90 situated in the first region is permitted (Even when the start of the treatment is permitted, the treatment is not started unless a prescribed condition, such as priority of the contents of the treatment, is satisfied.).

Figure 10A:
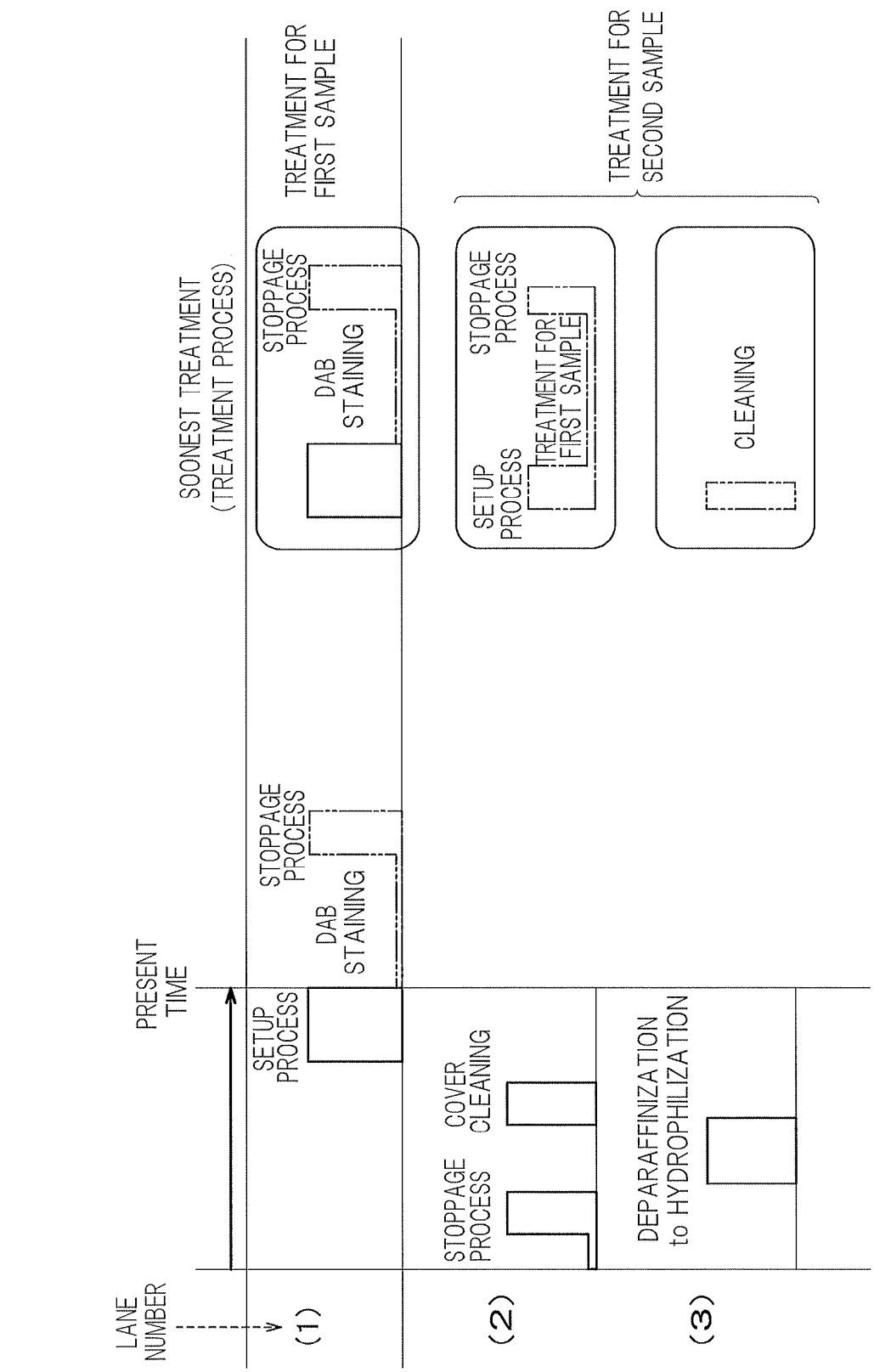
FIG. 10A is a diagram showing an example of usage modes and usage schedules of the horizontal direction movement unit compared by the automatic tissue staining device according to the embodiment of the present invention.
Figure 10B:
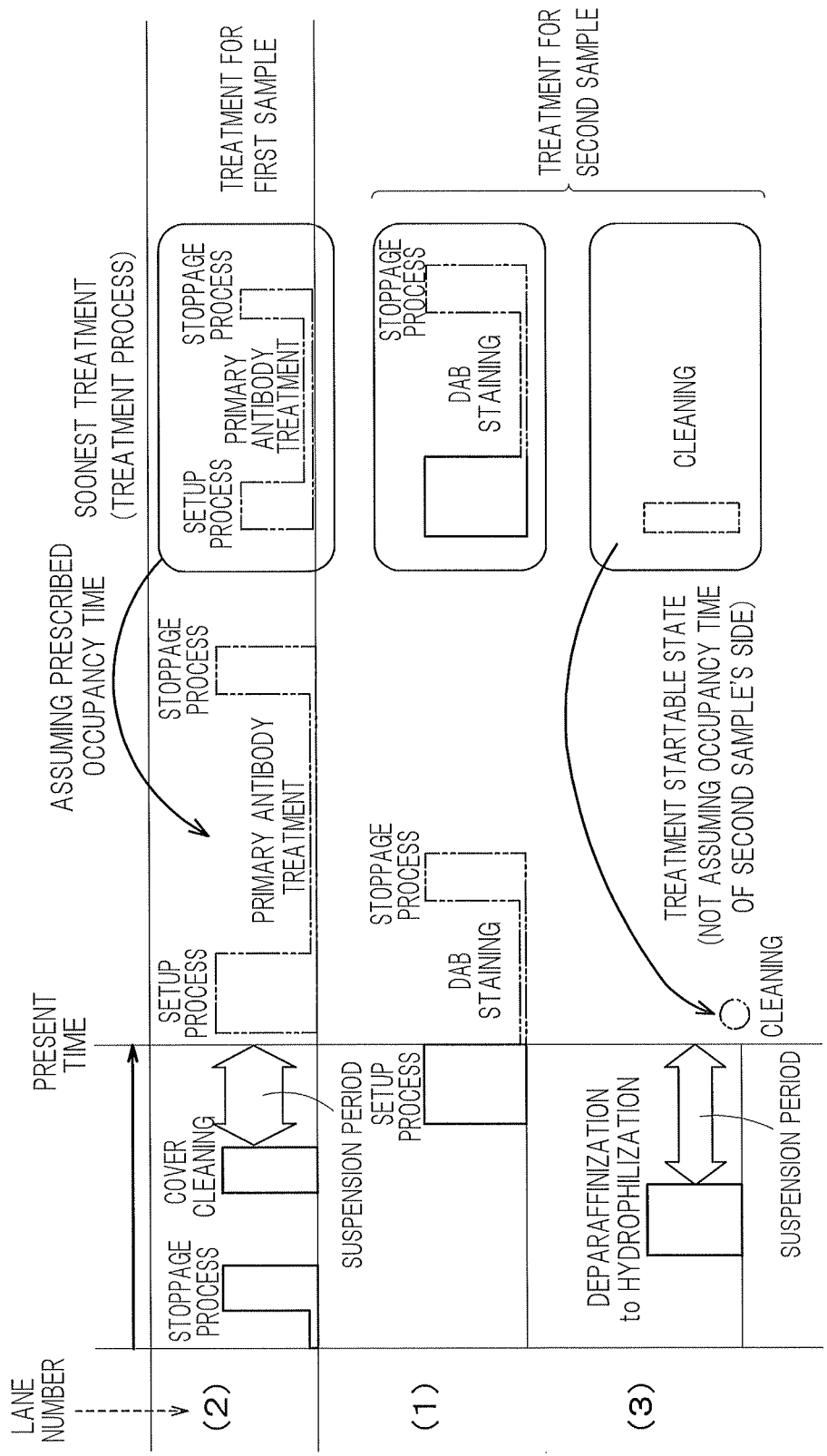
FIG. 10B is a diagram corresponding to FIG. 10A, FIG. 10B showing a case where samples on a lane (2) are handled as first samples at a time point slightly after a time point shown in FIG. 10A.
Figure 10C:
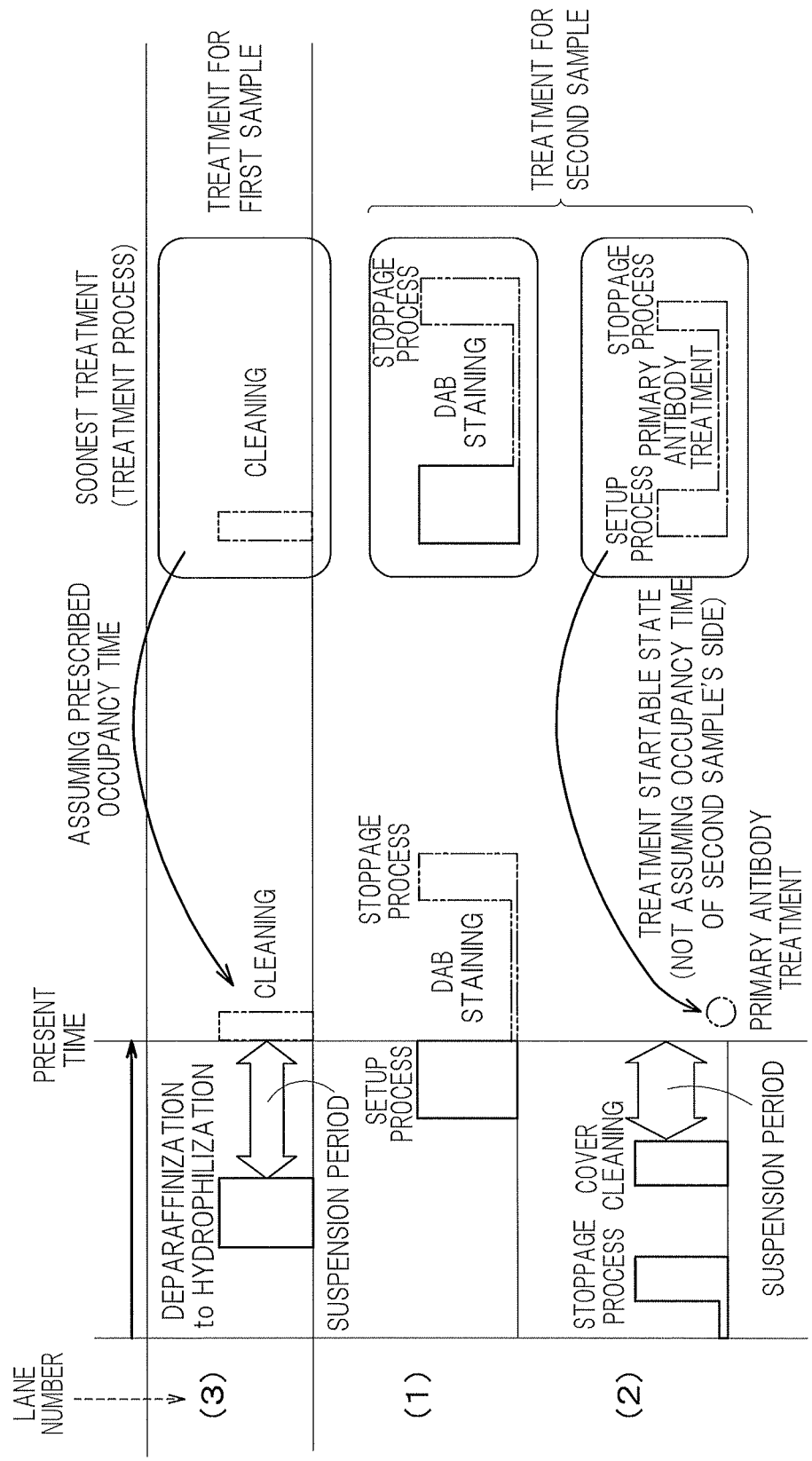
FIG. 10C is a diagram corresponding to FIG. 10A, FIG. 10C showing a case where samples on a lane (3) are handled as the first samples at a time point slightly after the time point shown in FIG. 10B.

When a reaction upon second samples on glass slides 90 situated in the second region has been started and a treatment of stopping the reaction upon the second samples is scheduled to be performed, the control unit 50 to 55 makes a comparison between a usage schedule of the horizontal direction movement unit 10 in a case where a treatment for first samples on glass slides 90 situated in the first region is started and a usage schedule of the horizontal direction movement unit 10 in the treatment for one or more of the second samples for which the treatment of stopping the reaction is scheduled (hereinafter referred to as a "reaction stoppage-scheduled second sample(s)") and thereby judges whether or not there is an overlap between the times of using the horizontal direction movement unit 10 in the case where the treatment for the first samples is started and the times of using the horizontal direction movement unit 10 in the treatment (including not only stoppage of a treatment process which will be explained later but also supplementation of a buffer solution, the same goes for the following explanation) for the reaction stoppage-scheduled second samples (see FIGS. 10B to 10D).

The mode of comparing usage schedules will be explained more specifically below. When a reaction upon second samples has been started and a treatment of stopping the reaction upon the second samples is scheduled to be performed, the control unit 50 to 55 compares treatment schedules from the present time in integrated process sequences (explained later, see FIG. 8) which are generated for the respective lane 6 with each other, thereby makes a comparison between a usage schedule of the horizontal direction movement unit 10 in a case where a treatment for a plurality of first samples on glass slides 90 situated on a certain lane 6 is started and a usage schedule of the horizontal direction movement unit 10 in a treatment for a plurality of reaction stoppage-scheduled second samples situated on another lane 6, and thereby judges whether or not there is an overlap between the times of using the horizontal direction movement unit 10 in the case where the treatment for the plurality of first samples is started and the times of using the horizontal direction movement unit 10 in the treatment for the plurality of reaction stoppage-scheduled second samples. Incidentally, the integrated process sequence is generated by integrating the treatment processes (explained later) for a plurality of samples held in the holding unit 7 on each lane 6.

The times of occupying the horizontal direction movement unit 10 and the times of using the horizontal direction movement unit 10 are judged by aggregating the processes in the integrated process sequence to some extent. More specifically, each treatment process for which a fixed reaction time is set (see antigen retrieval treatment, primary antibody reaction treatment, secondary antibody reaction treatment, DAB coloring treatment and nuclear staining treatment which will be explained later) includes a setup process of preparing for starting a reaction and a stoppage process of ending the reaction (see FIG. 9A). In the setup process, the horizontal direction movement unit 10 is judged to be continuously occupied or to be scheduled to be used. Similarly, also in the stoppage process, the horizontal direction movement unit 10 is judged to be continuously occupied or to be scheduled to be used. In contrast, in the case of a treatment process for which no fixed reaction time is set (see deparaffinization treatment, etc. which will be explained later), the treatment process is not particularly separated and the horizontal direction movement unit 10 is judged to be continuously occupied or judged to be scheduled to be used during the treatment process. Incidentally, supplementation of a buffer solution is conducted during the antigen retrieval treatment as will be explained later, and thus the antigen retrieval treatment includes not only the aforementioned setup process and stoppage process but also a supplementation process of supplementing a buffer solution. The stoppage process is started when a time accumulation value counted by the computation unit 44 reaches a prescribed time in regard to one of all the glass slides 90 whose reaction is ended by the stoppage process.

The computation unit 44 shown in FIG. 3 is configured to judge that the temperature of the sample has reached a prescribed temperature based on the result of measurement by the temperature measurement unit 21, start the counting based on time, and thereby perform the time accumulation. Further, in the antigen retrieval treatment which will be explained later, the computation unit 44 stops the aforementioned counting when the sample on the glass slide 90 is supplemented with a buffer solution as a type of treatment liquid, and restarts the aforementioned counting when the temperature is judged to have reached a prescribed temperature after the supplementation of the buffer solution. While the description of this embodiment is given by using such a mode in which the computation unit 44 serves as the "accumulation unit" described in claims, this embodiment is not limited to such a mode. For example, the accumulation unit may be provided separately from the computation unit 44.

When a treatment for the first samples can be started, the control unit 50 to 55 judges whether or not the soonest treatment for the second samples can be started. If the soonest treatment for the second samples can be started, the control unit 50 to 55 makes a comparison between the contents of the soonest treatment schedule for the first samples and the contents of the soonest treatment schedule (startable treatment schedule) for the second samples (see FIGS. 10B to 10D). Incidentally, such a comparison is not made in the case shown in FIG. 10A since FIG. 10A shows a case where a treatment for the first samples cannot be started.

When a treatment for the first samples can be started and a treatment for second samples cannot be started and there is no overlap between the times of using the horizontal direction movement unit 10 in the treatment schedule in the case where the treatment for the first samples is started and the times of using the horizontal direction movement unit 10 in the treatment schedule for the reaction stoppage-scheduled second samples, the control unit 50 to 55 permits the start of the treatment for the first samples. In contrast, when a treatment for the first samples can be started and the soonest treatment for second samples can be started (in this case, if both treatments are started, an overlap occurs between the times of using the horizontal direction movement unit 10 in the former treatment and the times of using the horizontal direction movement unit 10 in the latter treatment) or when there is an overlap between the times of using the horizontal direction movement unit 10 in the case where the treatment for the first samples is started and the times of using the horizontal direction movement unit 10 in the treatment for the reaction stoppage-scheduled second samples, the control unit 50 to 55 makes a comparison between the contents of the treatment schedule for the first samples and the contents of the treatment schedule for the second samples in the overlapping time.

In this embodiment, in regard to the treatment process including the soonest treatment for the first samples, it is possible to grasp not only whether the treatment process can be started or not but also the usage schedule of the horizontal direction movement unit 10 in the case where the treatment process is started, as shown in FIGS. 10A to 10D. Further, in cases where a reaction upon second samples has been started and it's been scheduled to perform a treatment of stopping the reaction or a buffer solution supplementation process upon the second samples, it is possible to grasp not only whether the treatment or process (in the case of the treatment of stopping the reaction, the stoppage process) can be started or not but also the usage schedule of the horizontal direction movement unit 10 in the stoppage process and the buffer solution supplementation process as shown in FIGS. 10B to 10D (the buffer solution supplementation process is not shown in FIGS. 10B to 10D) even when the treatment or process cannot be started yet. Incidentally, in regard to processes other than the buffer solution supplementation process or the stoppage process for the second samples, the control unit 50 to 55 judges only whether or not the treatment for the second samples can be started.

When a treatment for the first samples can be started and a treatment for second samples can be started (in this case, if both treatments are started, an overlap occurs between the times of using the horizontal direction movement unit 10 in the former treatment and the times of using the horizontal direction movement unit 10 in the latter treatment) or when there is an overlap between the times of using the horizontal direction movement unit 10 in the case where the treatment for the first samples is started and the times of using the horizontal direction movement unit 10 in the treatment for the reaction stoppage-scheduled second samples (i.e., the "stoppage process" or the "buffer solution supplementation process"), the control unit 50 to 55 makes a comparison between the contents of the treatment schedule for the first samples and the contents of the treatment schedule for the second samples in the overlapping time.

Incidentally, in FIGS. 10A to 10D, the horizontal direction movement unit 10 is scheduled to be used in times indicated by upward convexities. In contrast, for each treatment indicated by a circle (open circle) in FIGS. 10B to 10D, the occupancy time has not been assumed and the judgment is made only on whether or not the treatment can be started.

The usage schedule of the horizontal direction movement unit 10 in this embodiment is a schedule provisionally calculated in the generation of the integrated process sequence, by using standard treatment times in regard to each set of processes aggregated to some extent (as mentioned earlier). More specifically, after the present time in FIGS. 10A to 10D, the length of each part indicated as "SETUP PROCESS," "STOPPAGE PROCESS" or a concavity connecting between "SETUP PROCESS" and "STOPPAGE PROCESS" was provisionally calculated by using the standard treatment times.

Parenthetically, even when a reaction time is specified for a treatment process, in cases where the reaction time is short and the "fixed reaction time (specified reaction time)" (e.g., one minute) is not set, the reaction time includes almost no time in which the horizontal direction movement unit 10 is usable, and thus the treatment process is not separated into the "setup process" and the "stoppage process" and the horizontal direction movement unit 10 is judged to be scheduled to be used continuously in the treatment process. The deparaffinization treatment can be taken as an example of such a mode.

Further, as will be explained later, either the first samples or the second samples may include a plurality of samples for which different inspection methods are employed as long as their attributes are the same. For example, in cases where the first samples include a plurality of samples differing in the setting of the reaction time, the "stoppage process" can exist for each of the samples differing in the setting of the reaction time. In FIGS. 10A to 10D, the "stoppage process" is indicated as one convexity for either the first samples or the second samples, because it is supposed that in these cases the samples are identical in the setting of the reaction time.

When the treatment for the first samples can be started, a judgment is made on whether the contents of the treatment schedule for the first samples have priority over the contents of the treatment schedule for the second samples or not as a result of a comparison between the contents of the treatment schedule for the first samples and the contents of the treatment schedule for the second samples in the overlapping time. In this case, whether the treatment for the second samples can be started or not is also judged, and if the treatment for the second samples can be started, a judgment is made also on whether or not the contents of the soonest treatment schedule for the first samples have priority over the contents of the soonest treatment schedule for the second samples (startable treatment schedule). If the contents of the treatment schedule for the first samples have priority over the contents of the treatment schedule for the second samples, the soonest treatment for the first samples using the horizontal direction movement unit 10 is started. In contrast, if the contents of the treatment schedule for the second samples have priority over the contents of the treatment schedule for the first samples, the start of the soonest treatment for the first samples using the horizontal direction movement unit 10 is suspended.

When the start of the soonest treatment for the first samples using the horizontal direction movement unit 10 is suspended (e.g., the case of FIG. 10A), the samples that have been the first samples so far (in FIG. 10A, samples on the glass slides 90 situated on the lane 6 of the lane number (1)) are immediately changed into second samples and the samples that have been the second samples so far (in FIG. 10A, samples on the glass slides 90 situated on the lane 6 of the lane number (2)) are immediately changed into first samples, and then the comparison is made in a similar manner (FIG. 10B). When there are three lanes, there occur three combinations of the first samples and the second samples, and thus the comparison is made three times at the maximum. Among FIGS. 10A to 10C, FIG. 10A shows a progress in which the samples on the glass slides 90 situated on the lane 6 of the lane number (1) were handled as the first samples, it was impossible to start the treatment for the samples in that situation, and thus the comparison with the second samples was not made. FIG. 10B shows a progress in which the samples on the glass slides 90 situated on the lane 6 of the lane number (2) were handled as the first samples, it was possible to start the treatment for the samples in that situation, and thus the comparison with the second samples was made, but the start of the treatment for the first samples was suspended. FIG. 10C shows a progress in which the samples on the glass slides 90 situated on the lane 6 of the lane number (3) were handled as the first samples, it was possible to start the treatment for the samples in that situation, and thus the comparison with the second samples was made, and the treatment for the samples was started. In contrast, FIG. 10D shows an example in which the samples on the glass slides 90 situated on the lane 6 of the lane number (1) were handled as the first samples, the treatment (for the first samples) was started, and thus the comparison was made only once.

Incidentally, it is also possible to limit the ranges of the treatment schedules compared with each other by making a comparison between the usage schedule of the horizontal direction movement unit 10 in one or more treatments in the treatment process including the soonest treatment for the first samples and the usage schedule of the horizontal direction movement unit 10 in one or more treatments in the treatment process including the soonest treatment for the second samples. However, even with such limitation of the ranges of the compared treatment schedules, there can be cases where the overlap between the times of using the horizontal direction movement unit 10 occurs multiple times. In such cases, there can arise a judgment that the first samples have priority over the second samples in one of multiple treatments but the second samples have priority over the first samples in another one of the multiple treatments and there can be cases where for which samples the treatment should be started cannot be determined even by making the comparison for the maximum number of times (as shown in FIGS. 10A to 10C). When the treatment for the second samples can be started in such cases, there is a danger that even if the treatments for all the samples are suspended, the same situation is maintained also in the next check (e.g., 1/100 seconds later), the comparison result remains the same, and the treatments remain without proceeding. Therefore, in this embodiment, in such cases where the overlap between the times of using the horizontal direction movement unit 10 occurs multiple times, the comparison between treatment schedules is made only for the first overlap.

In this embodiment, as a first priority rule, when the contents of the treatment schedule for the first samples are a treatment of stopping the reaction upon the first samples and the contents of the treatment schedule for the second samples are a treatment other than a treatment of stopping the reaction upon the second samples, the contents of the treatment schedule for the first samples are prioritized over the contents of the treatment schedule for the second samples (in FIG. 10D, the samples on the glass slides 90 situated on the lane 6 of the lane number (1) are prioritized).

As a second priority rule, when the contents of the treatment schedules for the first samples and the second samples are treatments other than treatments of stopping the reactions upon the first samples and the second samples and the time for which the soonest treatment to be performed for the first samples (i.e., samples on the glass slides 90 situated on the lane 6 that is going to be treated from now) by using the horizontal direction movement unit 10 has been suspended is longer than the time for which the soonest treatment to be performed for the second samples (i.e., samples on the glass slides 90 situated on the remaining two lanes 6) by using the horizontal direction movement unit 10 has been suspended, the contents of the (soonest) treatment schedule for the first samples are prioritized over the contents of the (soonest) treatment schedule for the second samples (FIG. 10B and FIG. 10C). In passing, the suspension time for a treatment not in the startable state remains at "0."

Incidentally, when there exists a sample for which an immunostaining method has been specified as the staining method and the contents of the treatment schedule for the first samples are a treatment of stopping the reaction upon the first samples and the contents of the treatment schedule for the second samples are also a treatment of stopping the reaction upon the second samples, the contents of the treatment schedule for the first samples are prioritized over the contents of the treatment schedule for the second samples if the contents of the treatment schedule for the first samples are a treatment of stopping a reaction of a "primary antibody" upon an antigen in the first samples and the contents of the treatment schedule for the second samples are a treatment other than a treatment of stopping a reaction of a "primary antibody" upon an antigen in the second samples.

Further, when the contents of the treatment schedule for the first samples are a treatment of stopping the reaction upon the first samples and the contents of the treatment schedule for the second samples are also a treatment of stopping the reaction upon the second samples, the contents of the treatment schedule for the first samples are prioritized over the contents of the treatment schedule for the second samples if the reaction time specified for the first samples being stoppage targets is shorter than the reaction time specified for the second samples being stoppage targets.

Next, the operational unit database 82, the inspection procedure database 81, etc. shown in FIG. 4 will be explained in more detail. Each "unit," corresponding to an "operational unit" stored in the operational unit database 82 shown in FIG. 4 is in a state in which no parameter has been registered yet. The operational unit database 82 has stored items such as air blow (perform/none), cover attachment (perform/none), reagent dropping (needle/nozzle/manual/none), cover overflow cleaning (buffer solution: once/twice/three times/four times/five times/six times, water: once/twice/three times/four times/five times/six times), cover detachment (perform/none), glass slide cleaning (none, buffer solution: once/twice/three times/four times/five times/six times, water: once/twice/three times/four times/five times/six times) and fluid drainage (none/ordinary/toxic/organic) as the "units." As will be explained later, the aforementioned "air blow" means a process of having the blow nozzles 75*c* and 75*d* blow gas such as air onto the glass slides 90, the covers 25, etc. The "overflow cleaning" means a process of supplying a buffer solution from above the cover 25 and thereby causing a solution in a liquid pool between the glass slide 90 and the under surface of the cover 25 to be pushed out, overflow, and be discharged through holes (not shown) at the four corners of the cover 25 cylindrically connecting from the under surface to the top surface of the cover 25.

A protocol corresponding to the "attribute" is generated by selecting and connecting "units" explained above. A protocol can be generated by, for example, connecting one or multiple units such as deparaffinization treatment 1 (without air blow, organic solvent dropping, without cleaning), deparaffinization treatment 2 (with air blow, organic solvent dropping, without cleaning), amphipathicity treatment 1 (with air blow, alcohol dropping, without cleaning), amphipathicity treatment 2 (with air blow, alcohol dropping, with cleaning), buffer cleaning, antigen retrieval (heating) (with use of the cover), antigen retrieval (enzyme) (without use of the cover), blocking treatment, first antibody treatment (with use of the cover), second antibody treatment (with use of the cover), DAB coloring treatment, nuclear staining treatment and ending treatment. The protocols generated as above are stored in the operation procedure attribute database 85.

Further, a detection system is generated by selecting such a protocol and registering parameters regarding each unit, such as whether or not to execute the unit (ON/OFF), reagent type (excluding antigen retrieval reagents and first antibody reagents), reaction time and reaction temperature (i.e., the temperature of the heating unit 20). The detection systems generated as above are stored in the intermediate database 88 connected to the inspection procedure database 81 and the operation procedure attribute database 85 as shown in FIG. 4. Incidentally, a plurality of detection systems can be registered for the same protocol. In this embodiment, detection systems of the same protocol are judged to be identical in the "attribute." Parenthetically, in this embodiment, the antigen retrieval treatment is determined depending on the type of the first antibody. Since the number of types of first antibodies becomes extremely large, the parameters have not been specified yet in regard to antigen retrieval reagents and first antibody reagents at the stage of generating the detection system.

In the inspection procedure database 81, staining programs corresponding to the "inspection methods" are stored. The staining program is generated by selecting a particular detection system, specifying a first antibody to be used in the selected particular detection system, and registering the specified first antibody in the inspection procedure database 81. Specifically, the operator first selects a registered first antibody reagent from a first antibody registration screen displayed on the display unit 42 of the operation monitoring device 40 and registers corresponding parameters (reaction time, reaction temperature and the presence/absence (ON/OFF) of the antigen retrieval treatment). Then, when the antigen retrieval (heating) treatment is set "ON," the operator registers its conditions (activation reagent type, reaction time and reaction temperature). When the antigen retrieval (enzyme) treatment is set "ON," the operator registers its conditions (activation reagent type, reaction time and reaction temperature). When both the antigen retrieval (heating) treatment and the antigen retrieval (enzyme) treatment are set "ON," the operator registers their respective conditions. Incidentally, if staining programs generated as above have the same protocol, the staining programs are judged to be identical in the "attribute."

<<Method>>

Next, the flow of treatments performed on samples in the automatic tissue staining method using the above-described automatic tissue staining device 100 will be described briefly. See FIG. 11 for the order of treatment processes.

[Deparaffinization Treatment]

First, an organic solvent is supplied from the organic solvent nozzle 75b (see FIG. 6) to the samples on the glass slides 90, by which paraffin surrounding the samples is eluted and removed. After the elution of paraffin, alcohol is supplied from the organic solvent nozzle 75b to the samples on the glass slides 90 and the surfaces of the samples are made amphipathic. Thereafter, a buffer solution is supplied from the buffer solution nozzle 75a to the samples on the glass slides 90 to replace alcohol.

Parenthetically, in the initial stage, a sample was embedded in paraffin, thereafter sliced into thin slices of samples, and affixed on glass slides 90. However, since the paraffin is hydrophobic, the surfaces of the samples have also become hydrophobic and that hinders the subsequent treatments. The deparaffinization treatment described above is performed for this reason.

[Blocking Treatment]

Subsequently, a blocking solution made of a hydrogen peroxide solution or the like is sucked in from a reagent vessel 91 by the reagent needle 76 (see FIG. 6) and dropped onto samples on glass slides 90 as targets of treatment, by which peroxidase or the like contained in the samples is deactivated. After the deactivation of peroxidase or the like, the samples are cleaned by supplying a buffer solution from the buffer solution nozzle 75a to the samples on the glass slides 90. Even when a reaction or the like is in progress, the reaction can be stopped by supplying a buffer solution to the samples as above. The same goes for treatments explained below.

Such a blocking treatment is performed for the following reason: The purpose of the inspection is to visualize peroxidase or the like, that has labeled the secondary antibody, by a method such as DAB coloring in order to stain the positions where the antigen as the inspection target exists. However, there are cases where peroxidase or the like exists also in the tissue containing the antigen. If such peroxidase or the like also develops color, a false-positive result can occur. In this regard, the occurrence of such a false-positive result can be prevented by performing the blocking treatment.

Incidentally, when different liquids are discharged by using the same liquid supply nozzle 75a or 75b (i.e., the buffer solution nozzle 75a or the organic solvent nozzle 75b), the aforementioned preliminary discharge is performed by the water jet cleaning unit 26 situated at the initial position of the horizontal direction movement unit 10. The preliminary discharge is performed also in each treatment explained below even if it is not specifically described. Parenthetically, in cases where the antigen flows out due to the blocking treatment, the blocking treatment may be performed after the antigen retrieval treatment explained below.

[Antigen Retrieval Treatment]

Subsequently, a treatment of activating the antigen contained in the samples by heating is performed. Specifically, first, gas such as air is blown onto the glass slides 90 and the covers 25 (see FIG. 2) by the blow nozzles 75c and 75d (see FIG. 6) and the buffer solution on the glass slides 90 and the covers 25 is blown off and removed. At that time, the temperature measured by the temperature measurement units 21 has fallen to 35° C. or below, for example. Subsequently, upper surfaces of the glass slides 90 are covered with the covers 25, the glass slides 90 are moved downward, and lower surfaces of the glass slides 90 are brought to close contact with the heating units 20. In this state, the holding unit 7 receives upward biasing force from the elastic members 6a (see FIG. 5). Thereafter, the buffer solution is supplied from the buffer solution nozzle 75a to the covers 25 (see FIG. 2). Thereafter, the temperature of each heating unit 20 is raised and when the temperature of the sample is judged to have reached a prescribed temperature based on the measurement by the temperature measurement unit 21, the temperature is maintained. Incidentally, a uniform liquid pool is formed between the glass slide 90 and the under surface of the cover 25 due to the inflow of the buffer solution to the cover 25 from above.

When the temperature of the sample is judged to have reached the prescribed temperature, the computation unit 44 (see FIG. 3) starts the time count and performs the time accumulation. While the prescribed temperature is maintained as above, the supplementation of the buffer solution can become necessary in consideration of evaporation of the buffer solution. In such cases of supplementing the sample on the glass slide 90 with the treatment liquid by supplying the buffer solution to the cover 25, the computation unit 44 stops the time count regarding the time for which the prescribed temperature is reached, and restarts the time count when the temperature reaches the prescribed temperature after the supplementation of the treatment fluid (treatment liquid), or after a prescribed time (e.g., one minute) has passed since the supplementation of the treatment fluid.

When the time accumulated by the computation unit 44 reaches a prescribed time, the heating unit 20 turns to an OFF state. When the heating unit 20 is in the OFF state, the sample is naturally cooled down.

Then, when the sample is cooled down to approximately 65° C., for example, the cover 25 is cleaned by supplying the buffer solution from the buffer solution nozzle 75a to the cover 25 (see FIG. 2). In this case, the buffer solution flows into the cover 25 from above; however, the solution pushed out from the liquid pool between the glass slide 90 and the under surface of the cover 25 overflows and is discharged through the holes (not shown) at the four corners of the cover 25 cylindrically connecting from the under surface to the top surface of the cover 25. By having the buffer solution overflow as above, the buffer solution after being used for the antigen retrieval can be replaced and the temperature of the sample can be lowered efficiently. After supplying the buffer solution to the cover 25 as above, the cover 25 may be left untouched for a prescribed time (e.g., two minutes) to promote heat radiation. When the cover 25 has been cleaned as above and has reached a prescribed temperature (e.g., 45° C.), the lock of the cover 25 is released by the cover opening/closing air cylinder 57 and the twelve covers 25 are pivoted upward and opened around a shaft (not shown) extending in the depth direction of the housing 1. Accordingly, by the biasing force the holding unit 7 receives from the elastic members 6a, the glass slides 90 are elevated, the close contact with the heating units 20 is released, and the heat radiation is promoted further. Then, the supply head 11 is moved by the horizontal direction movement unit 10 to draw a U-shape as viewed from above, and the under surfaces of the covers 25 and at least parts of the glass slides 90 that have been in contact with the under surfaces of the covers 25 are cleaned. After supplying the buffer solution to the covers 25 and the glass slides 90 as above, the covers 25 and the glass slides 90 may be left untouched for a prescribed time (e.g., two minutes) to promote heat radiation. Thereafter, natural heat radiation is continued and the antigen retrieval treatment is ended when the temperature measured by the temperature measurement units 21 has fallen to 35° C. or below.

Incidentally, the above-described cleaning of the covers 25 and the glass slides 90 is performed similarly also in the primary antibody reaction treatment and the secondary antibody reaction treatment which will be explained later.

The antigen retrieval treatment described above is performed for the following reason: The antigen in the sample has undergone crosslinkage due to the formalin fixation, and thus is in a state in which the reaction with the primary antibody explained later is unlikely to occur. In this regard, performing the above-described antigen retrieval treatment facilitates the primary antibody explained later to react with the antigen. As an example of the antigen retrieval treatment, it is possible to use a buffer solution containing a chelating agent for removing metallic ions and continue heating the sample (antigen) at a prescribed temperature for approximately one hour.

Figure 9A:
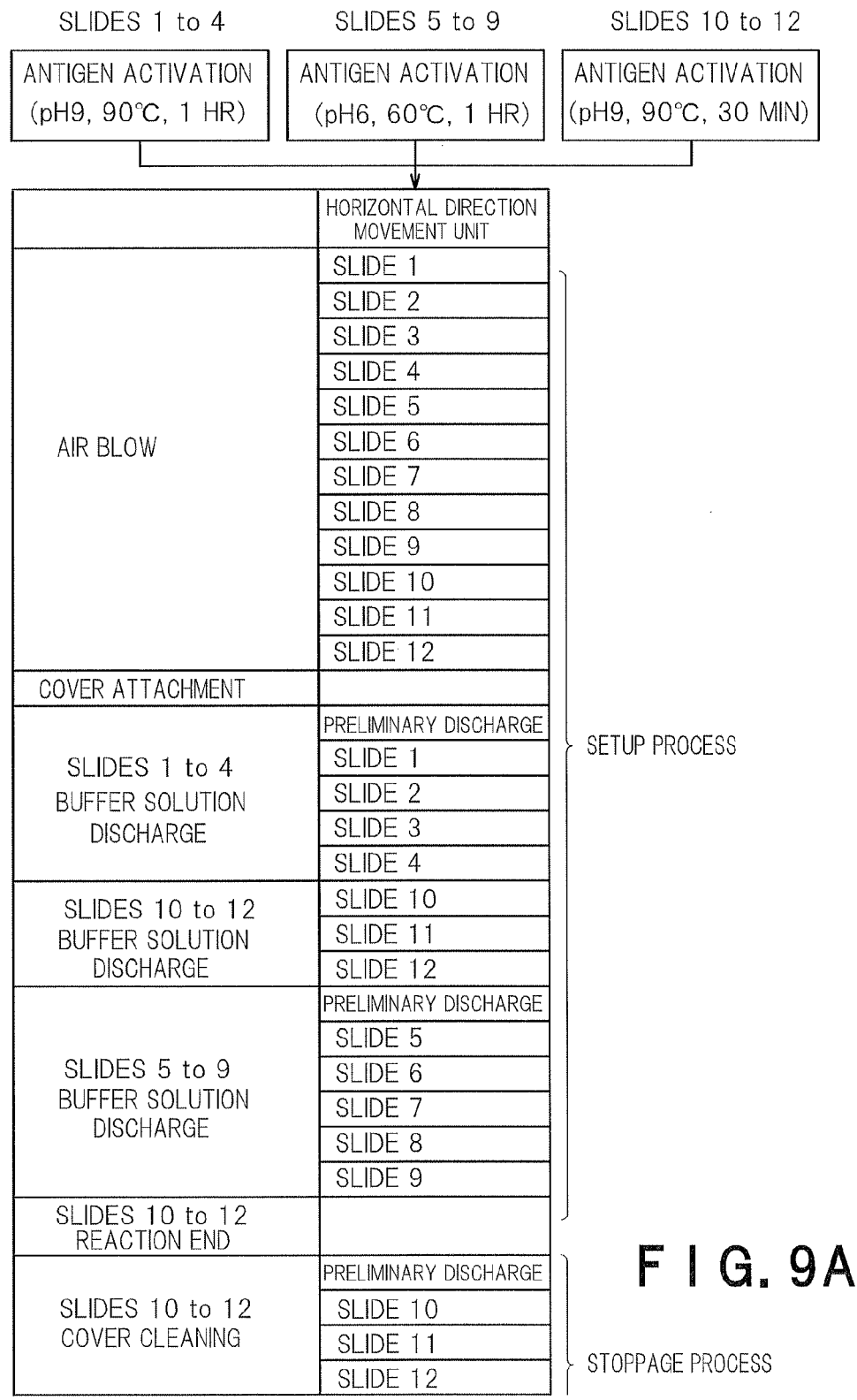
FIG. 9A is a diagram showing the part of the integrated process sequence shown in FIG. 8 while separating the part into a setup process and a stoppage process.

Parenthetically, in this antigen retrieval treatment, as shown in FIG. 9A, the process from blowing gas such as air onto the glass slides 90 and the covers 25 with the blow nozzles 75c and 75d to supplying the buffer solution from the buffer solution nozzle 75a to the covers 25 is the "setup process," and the process from performing the preliminary discharge of the buffer solution nozzle 75a after the heating units 20 turned OFF to the cleaning of the glass slides 90 and the covers 25 is the "stoppage process." Incidentally, the reason why the processes from blowing gas such as air onto the glass slides 90 and the covers 25 with the blow nozzles 75c and 75d to supplying the buffer solution from the buffer solution nozzle 75a to the covers 25 are performed quickly in succession is that the samples blown with gas have become dry and have to be supplied with the buffer solution in a short time.

Figure 9B:
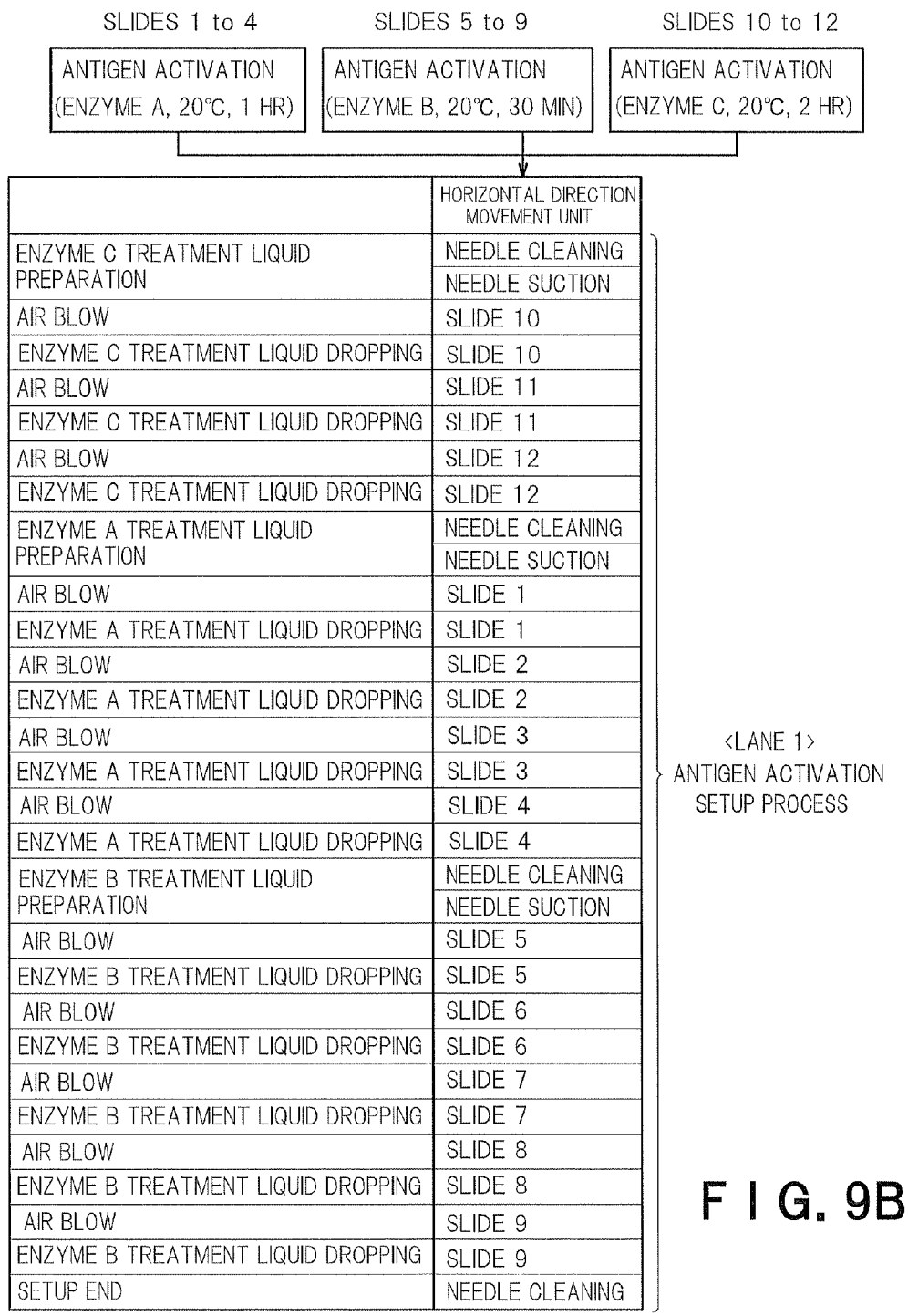
FIG. 9B is a diagram showing an example of a part of an integrated process sequence (a part corresponding to a part of an antigen retrieval treatment process using enzymes) generated by the automatic tissue staining device according to the embodiment of the present invention.

When the integrated process sequence for each lane 6 is generated, in regard to an antigen retrieval treatment using an enzyme, a sequence for the antigen retrieval treatment like the one shown in FIG. 9B is generated and the generated sequence becomes a part of the integrated process sequence of the lane 6. More specifically, the following sequence is generated for slides 1 to 12 on a certain lane 6 ("LANE 1" in FIG. 9B): First, the reagent needle 76 is cleaned by the water jet cleaning unit 26 and thereafter a prescribed amount of an enzyme C is sucked in by the reagent needle 76. Subsequently, gas such as air is blown onto a targeted glass slide 90 (slide 10) by the blow nozzles 75c and 75d to blow off and remove the buffer solution on the glass slide 90, and thereafter the enzyme C is dropped onto the targeted glass slide 90 (slide 10). Then, for glass slides 90 using the same enzyme C (slides 11 and 12), the air blow and the dropping of the enzyme C are performed sequentially. When a different enzyme A is used, the supply head 11 moves to a position over the water jet cleaning unit 26, the reagent needle 76 is cleaned by the water jet cleaning unit 26, and thereafter a prescribed amount of the enzyme A is sucked in by the reagent needle 76. Subsequently, the supply head 11 moves to a position over a prescribed reagent vessel 91, the reagent needle 76 sucks in the targeted enzyme A from the reagent vessel 91, and thereafter a process equivalent to the above-described process is performed repeatedly. After the enzyme dropping treatment is finished, the reagent needle 76 is cleaned.

[Primary Antibody Reaction Treatment]

After the antigen retrieval treatment is finished, a treatment of having the primary antibody attach to the antigen contained in the sample is performed next. Specifically, first, gas such as air is blown onto the glass slides 90 and the covers 25 by the blow nozzles 75c and 75d and the buffer solution on the glass slides 90 and the covers 25 is blown off and removed. At that time, the temperature measured by the temperature measurement units 21 has fallen to 35° C. or below, for example. By removing the buffer solution as above, the reagent or the like supplied next can be prevented from being diluted by the remaining buffer solution (The same effect can be achieved also in the blocking treatment and the antigen retrieval treatment explained above and the secondary antibody reaction treatment, the DAB coloring treatment and the nuclear staining treatment which will be explained later.). Subsequently, the upper surfaces of the glass slides 90 are covered with the covers 25, the glass slides 90 are moved downward, and the lower surfaces of the glass slides 90 are brought to close contact with the heating units 20. At that time or thereafter, the supply head 11 moves to the position over the water jet cleaning unit 26 and the reagent needle 76 is jet-cleaned by the water jet cleaning unit 26. At that time, the reagent needle 76 sucks in a small amount of buffer solution and further sucks in a small amount of air. Subsequently, the supply head 11 moves to a position over a prescribed reagent vessel 91 and the reagent needle 76 sucks in a reagent from the reagent vessel 91. In this case, the reagent needle 76 is moved to a prescribed position by a vertical direction drive unit and thereafter sucks in a prescribed amount of the reagent from the reagent vessel 91. The air sucked in as mentioned above serves as an air gap in the pipe of the reagent needle 76 and prevents the sucked reagent from mixing with the aforementioned buffer solution already sucked in.

Subsequently, the supply head 11 moves to a position over a prescribed glass slide 90 and the reagent needle 76 drops a specified amount of the sucked reagent from above the cover 25. In cases where the same reagent is dropped onto a plurality of glass slides 90, the same reagent is dropped consecutively based on one suction by the reagent needle 76. Such consecutive supply of the reagent by the reagent needle 76 is continued to an extent not exceeding the capacity of the syringe (not shown) supplying the reagent to the reagent needle 76.

Before and after using the reagent needle 76, the jet cleaning of the reagent needle 76 is carried out without omission by the water jet cleaning unit 26. As mentioned earlier, the cleaning of the reagent needle 76 is performed by first discharging all of the liquid in the reagent needle 76 including the aforementioned buffer solution sucked in. Then, the reagent needle 76 sucks in a prescribed amount of cleaning liquid until the cleaning liquid reaches the inside of the syringe (not shown) connected to the reagent needle 76 and thereafter discharges the cleaning liquid. The suction and discharge of the cleaning liquid are repeated multiple times. However, when the same reagent is dropped onto a plurality of glass slides 90, the jet cleaning of the reagent needle 76 is conducted after finishing the dropping of the reagent onto those glass slides 90. Such jet cleaning of the reagent needle 76 is conducted similarly also in the blocking treatment and the antigen retrieval treatment using an enzyme which have been explained above and the secondary antibody reaction treatment, the DAB coloring treatment and the nuclear staining treatment which will be explained later even if it is not specifically described.

After the specified amount of the reagent is dropped onto the cover 25 as above, the temperature of the heating unit 20 is raised (for approximately 10 seconds, for example) and when the temperature of the sample is judged to have reached a prescribed temperature (e.g., approximately 25°

C. to 45° C.) based on the measurement by the temperature measurement unit 21, the temperature is maintained. When the temperature of the sample is judged to have reached the prescribed temperature as above, the computation unit 44 starts the counting based on time and performs the time accumulation. When the time accumulated by the computation unit 44 reaches a prescribed time, the heating unit 20 is turned to the OFF state. Around or at the time when the heating unit 20 is turned to the OFF state, the cover 25 is cleaned by supplying the buffer solution from the buffer solution nozzle 75a to the cover 25. In this case, the buffer solution flows into the cover 25 from above; however, the solution pushed out from the liquid pool between the glass slide 90 and the under surface of the cover 25 overflows and is discharged through the holes at the four corners of the cover 25 cylindrically connecting from the under surface to the top surface of the cover 25. By supplying the buffer solution from the buffer solution nozzle 75a to the cover 25 as above, the reaction of the primary antibody upon the antigen is stopped. When the cover 25 has been cleaned and has reached to a prescribed temperature, the lock of the cover 25 is released by the cover opening/closing air cylinder 57 and the twelve covers 25 are pivoted upward and opened around the shaft extending in the depth direction of the housing 1. Then, the supply head 11 is moved by the horizontal direction movement unit 10 to draw a U-shape as viewed from above, and the under surfaces of the covers 25 and at least parts of the glass slides 90 that have been in contact with the under surfaces of the covers 25 are cleaned.

Parenthetically, in this primary antibody reaction treatment, the process from blowing gas such as air onto the glass slides 90 and the covers 25 with the blow nozzles 75c and 75d to dropping the reagent from above the covers 25 with the reagent needle 76 is the "setup process," and the process from performing the preliminary discharge of the buffer solution nozzle 75a just before stopping the primary antibody reaction to the cleaning of the glass slides 90 and the covers 25 is the "stoppage process."

[Secondary Antibody Reaction Treatment]

After the primary antibody reaction treatment is finished, a treatment of having the secondary antibody attach to the primary antibody that has bound to the antigen on the surface of the sample is performed next. This secondary antibody reaction treatment is performed similarly to the primary antibody reaction treatment described above. First, gas such as air is blown onto the glass slides 90 and the covers 25 by the blow nozzles 75c and 75d and the buffer solution on the glass slides 90 and the covers 25 is blown off and removed. At that time, the temperature measured by the temperature measurement units 21 has fallen to 35° C. or below, for example. Subsequently, the upper surfaces of the glass slides 90 are covered with the covers 25, the glass slides 90 are moved downward, and the lower surfaces of the glass slides 90 are brought to close contact with the heating units 20. At that time or thereafter, the supply head 11 moves to the position over the water jet cleaning unit 26 and the reagent needle 76 is jet-cleaned by the water jet cleaning unit 26. Subsequently, the supply head 11 moves to a position over a prescribed reagent vessel 91 and the reagent needle 76 sucks in a reagent from the reagent vessel 91. In this case, the reagent needle 76 is moved to a prescribed position by the vertical direction drive unit and thereafter sucks in a prescribed amount of the reagent from the reagent vessel 91.

Subsequently, the supply head 11 moves to a position over a prescribed glass slide 90 and the reagent needle 76 drops a specified amount of the sucked reagent from above the cover 25. In cases where the same reagent is dropped onto a plurality of glass slides 90, the same reagent is dropped consecutively based on one suction by the reagent needle 76.

After the specified amount of the reagent is dropped onto the cover 25 as above, the temperature of the heating unit 20 is raised and when the temperature of the sample is judged to have reached a prescribed temperature based on the measurement by the temperature measurement unit 21, the temperature is maintained. When the temperature of the sample is judged to have reached the prescribed temperature as above, the computation unit 44 starts the time count and performs the time accumulation. When the time accumulated by the computation unit 44 reaches a prescribed time, the heating unit 20 is turned to the OFF state after heating the sample. Around or at the time when the heating unit 20 is turned to the OFF state, the cover 25 is cleaned by supplying the buffer solution from the buffer solution nozzle 75a to the cover 25. In this case, the buffer solution flows into the cover 25 from above; however, the solution pushed out from the liquid pool between the glass slide 90 and the under surface of the cover 25 overflows and is discharged through the holes at the four corners of the cover 25 cylindrically connecting from the under surface to the top surface of the cover 25. By supplying the buffer solution from the buffer solution nozzle 75a to the cover 25 as above, the reaction of the secondary antibody upon the antigen is stopped. When the cover 25 has been cleaned and has reached to a prescribed temperature, the lock of the cover 25 is released by the cover opening/closing air cylinder 57 and the cover 25 is pivoted upward and opened around the shaft extending in the depth direction of the housing 1. Then, the supply head 11 is moved by the horizontal direction movement unit 10 to draw a U-shape as viewed from above, and the under surface of the cover 25 and at least a part of the glass slide 90 that has been in contact with the under surface of the cover 25 are cleaned.

Parenthetically, in this secondary antibody reaction treatment, the process from blowing gas such as air onto the glass slides 90 and the covers 25 with the blow nozzles 75c and 75d to dropping the reagent from above the covers 25 with the reagent needle 76 is the "setup process," and the process from performing the preliminary discharge of the buffer solution nozzle 75a just before stopping the secondary antibody reaction to the cleaning of the glass slides 90 and the covers 25 is the "stoppage process."

[DAB Coloring Treatment]

After the secondary antibody reaction treatment is finished, a treatment of DAB-coloring peroxidase or the like that has labeled the secondary antibody contained in the sample is performed next. Specifically, first, the supply head 11 moves to a position over a prescribed reagent vessel 91 and the reagent needle 76 sucks in a prescribed amount of a reagent from the reagent vessel 91. In this case, the reagent needle 76 is moved to a prescribed position by the vertical direction drive unit and thereafter sucks in the prescribed amount of the targeted reagent from the reagent vessel 91. Subsequently, gas such as air is blown onto the glass slides 90 by the blow nozzles 75c and 75d and the buffer solution on the glass slides 90 is blown off and removed. Thereafter, the reagent is dropped onto a targeted glass slide 90. At that time, the temperature measured by the temperature measurement unit 21 has fallen to 35° C. or below, for example. This process is performed repeatedly and when the reagent dropping treatment is finished, the reagent needle 76 is cleaned.

After the dropping of the reagent is finished, the temperature of the heating unit 20 is raised and when the temperature of the sample is judged to have reached a prescribed temperature based on the measurement by the temperature measurement unit 21, the temperature is maintained. When the temperature of the sample is judged to have reached the prescribed temperature as above, the computation unit 44 starts the time count and performs the time accumulation. When the time accumulated by the computation unit 44 reaches a prescribed time, the heating unit 20 is turned to the OFF state. Around or at the time when the heating unit 20 is turned to the OFF state, the glass slide 90 is cleaned by supplying the buffer solution from the buffer solution nozzle 75a to the glass slide 90. By supplying the buffer solution from the buffer solution nozzle 75a to the glass slide 90 as above, the reaction is stopped.

Incidentally, the reason why the buffer solution on the targeted glass slide 90 is blown off and removed just before dropping the specified amount of the sucked reagent onto the glass slide 90 as above is that the sample dries easily since the cover 25 is not used. Put another way, although the sample dries easily in the DAB coloring treatment since the cover 25 is not used, it is possible to prevent the sample from drying out by conducting the drying of the glass slide 90 just before the dropping of the reagent.

In this DAB coloring treatment, the process from jet-cleaning the reagent needle 76 with the water jet cleaning unit 26 to dropping the reagent from the reagent needle 76 onto the glass slides 90 is the "setup process," and the process from performing the preliminary discharge of the buffer solution nozzle 75a just before stopping the DAB coloring reaction to the cleaning of the glass slides 90 is the "stoppage process."

[Nuclear Staining Treatment]

After the DAB coloring treatment is finished, a treatment of staining the nuclei of the cells of the sample is performed next. Specifically, first, the supply head 11 moves to a position over a prescribed reagent vessel 91 and the reagent needle 76 sucks in a prescribed amount of a reagent from the reagent vessel 91. In this case, the reagent needle 76 is moved to a prescribed position by the vertical direction drive unit and thereafter sucks in the prescribed amount of the targeted reagent from the reagent vessel 91. Subsequently, gas such as air is blown onto the glass slides 90 by the blow nozzles 75c and 75d and the buffer solution on the glass slides 90 is blown off and removed. Thereafter, the reagent is dropped onto a targeted glass slide 90. This process is performed repeatedly and when the reagent dropping treatment is finished, the reagent needle 76 is cleaned.

After the dropping of the reagent is finished, the temperature of the heating unit 20 is raised and when the temperature of the sample is judged to have reached a prescribed temperature based on the measurement by the temperature measurement unit 21, the temperature is maintained. When the temperature of the sample is judged to have reached the prescribed temperature as above, the computation unit 44 starts the time count and performs the time accumulation. When the time accumulated by the computation unit 44 reaches a prescribed time, the heating unit 20 is turned to the OFF state. After the heating unit 20 is turned to the OFF state, the glass slide 90 is cleaned by supplying water such as pure water from the buffer solution nozzle 75a to the glass slide 90. By supplying water from the buffer solution nozzle 75a to the glass slide 90 as above, the reaction is stopped.

Also in the nuclear staining treatment, the reason why the buffer solution on the glass slide 90 is blown off and removed just before dropping the specified amount of the sucked reagent onto the targeted glass slide 90 is that the sample dries easily since the cover 25 is not used, as mentioned in the explanation of the DAB coloring treatment.

In this nuclear staining treatment, the process from jet-cleaning the reagent needle 76 with the water jet cleaning unit 26 to dropping the reagent from the reagent needle 76 onto the glass slides 90 is the "setup process," and the process from performing the water preliminary discharge of the buffer solution nozzle 75a just before stopping the nuclear staining reaction to the cleaning of the glass slides 90 is the "stoppage process."

Parenthetically, in the nuclear staining treatment, the staining time is rather short (e.g., approximately one minute). Thus, in such cases where the staining time in the nuclear staining treatment is short, the aforementioned sequence of processes may be performed quickly in succession. When such a mode is employed, the horizontal direction movement unit 10 is judged to be continuously occupied or to be scheduled to be used during the nuclear staining treatment.

[Generation of Integrated Process Sequence]

Next, a mode of generating the aforementioned integrated process sequence will be explained below.

The integrated process sequence is generated for each of a plurality of regions (lanes 6) and includes a sequence of treatment processes for a plurality of samples in the region. The integrated process sequence is generated on each lane 6 by comparing individual process sequences, each including a plurality of treatment processes performed for a corresponding one of the samples on a lane 6, with each other so as to consecutively perform treatment processes of the same contents on a plurality of samples on the lane 6. For example, as shown in FIG. 11, even when a group of glass slides $90_1$ to $90_4$, a group of glass slides $90_5$ to $90_9$ and a group of glass slides $90_{10}$ to $90_{12}$ included in the twelve glass slides 90 on a certain lane 6 differ from each other in the mode of treatment, the integrated process sequence is generated so that each of the treatment processes, namely, each of the deparaffinization treatment, the blocking treatment, the antigen retrieval treatment, the primary antibody reaction treatment, the secondary antibody reaction treatment, the DAB coloring treatment and the nuclear staining treatment, is performed on the glass slides $90_1$ to $90_{12}$ in the same period. By consecutively performing treatment processes having the same contents as above, the treatment efficiency can be increased. Parenthetically, in FIG. 11, for the glass slides $90_1$ to $90_4$, the antigen retrieval treatment is performed by using a buffer solution at pH9, at a reaction temperature of 90° C. and for a reaction time of one hour, the primary antibody reaction treatment is performed by having an antibody A react for one hour, and the secondary antibody reaction treatment is performed by having a polymer α react for 30 minutes. For the glass slides $90_5$ to $90_9$, the antigen retrieval treatment is performed by using a buffer solution at pH6, at a reaction temperature of 60° C. and for a reaction time of one hour, the primary antibody reaction treatment is performed by having an antibody B react for two hours, and the secondary antibody reaction treatment is performed by having the polymer α react for 30 minutes. For the glass slides $90_{10}$ to $90_{12}$, the antigen retrieval treatment is performed by using a buffer solution at pH9, at a reaction temperature of 90° C. and for a reaction time of 30 minutes, the primary antibody reaction treatment is performed by having an antibody C react for 30 minutes, and the secondary antibody reaction treatment is performed by having a polymer β react for one hour.

Further, the integrated process sequence is generated by comparing the contents of the treatment liquids (treatment fluids) supplied to the samples situated on the same lane 6 in the consecutively performed treatment processes of the same contents so as to consecutively treat samples that use the same treatment liquid (i.e., so that samples using the same treatment liquid are consecutively supplied with the treatment liquid). In the mode shown in FIG. 8 corresponding to the mode shown in FIG. 11, the same treatment liquid is used for the antigen retrieval treatment on the glass slides $90_1$ to $90_4$ and the glass slides $90_{10}$ to $90_{12}$, and the glass slides $90_5$ to $90_9$ use a treatment liquid different from the treatment liquid used for the glass slides $90_1$ to $90_4$ and the glass slides $90_{10}$ to $90_{12}$. By consecutively treating samples that use the same treatment liquid as above, the preliminary discharge, the jet cleaning of the reagent needle 76, etc. can be left out properly and the treatment efficiency can be increased. Parenthetically, in FIGS. 8, 9A and 9B, the glass slide $90_1$, the glass slide $90_2$, . . . , the glass slide $90_{11}$ and the glass slide $90_{12}$ are indicated as "SLIDE 1," "SLIDE 2," . . . , "SLIDE 11" and "SLIDE 12," respectively.

Furthermore, when the samples situated on the same lane 6 include a plurality of samples that use the same treatment liquid in the consecutively performed treatment processes of the same contents, the integrated process sequence is generated so as to supply the treatment liquid (treatment fluid) to a sample whose reaction time is long prior to a sample whose reaction time is short. By first supplying the treatment liquid to the sample whose reaction time is long as above, the treatment for the sample whose reaction time is long can be started early and the difference between the samples in the time of ending the treatment process can be reduced. In the mode shown in FIG. 8, the same treatment liquid is used for the antigen retrieval treatment on the glass slides $90_1$ to $90_4$ and the glass slides $90_{10}$ to $90_{12}$ as mentioned above. However, the reaction time on the glass slides $90_1$ to $90_4$ is "1 HR" whereas the reaction time on the glass slides $90_{10}$ to $90_{12}$ is "30 MIN," that is, the reaction time on the glass slides $90_1$ to $90_4$ is longer than the reaction time on the glass slides $90_{10}$ to $90_{12}$. Therefore, the buffer solution is supplied to the glass slides $90_1$ to $90_4$ prior to the glass slides $90_{10}$ to $90_{12}$.

Moreover, the integrated process sequence is generated so as to supply a treatment liquid (treatment fluid) to a sample whose reaction temperature is high prior to a sample whose reaction temperature is low. A sample whose reaction temperature is high takes a long time for the temperature rise and the temperature fall. By first supplying the treatment liquid (treatment fluid) to the sample whose reaction temperature is high as above, the treatment for the sample whose reaction temperature is high can be started early and the difference between the samples in the time of ending the treatment process can be reduced. In the mode shown in FIG. 8, the antigen retrieval treatment for the samples on the glass slides $90_1$ to $90_4$ and the glass slides $90_{10}$ to $90_{12}$ is performed at "90° C.," whereas the antigen retrieval treatment for the samples on the glass slides $90_5$ to $90_9$ is performed at "60° C." Therefore, the buffer solution is supplied to the glass slides $90_1$ to $90_4$ and the glass slides $90_{10}$ to $90_{12}$ prior to the glass slides $90_5$ to $90_9$.

Figure 8:
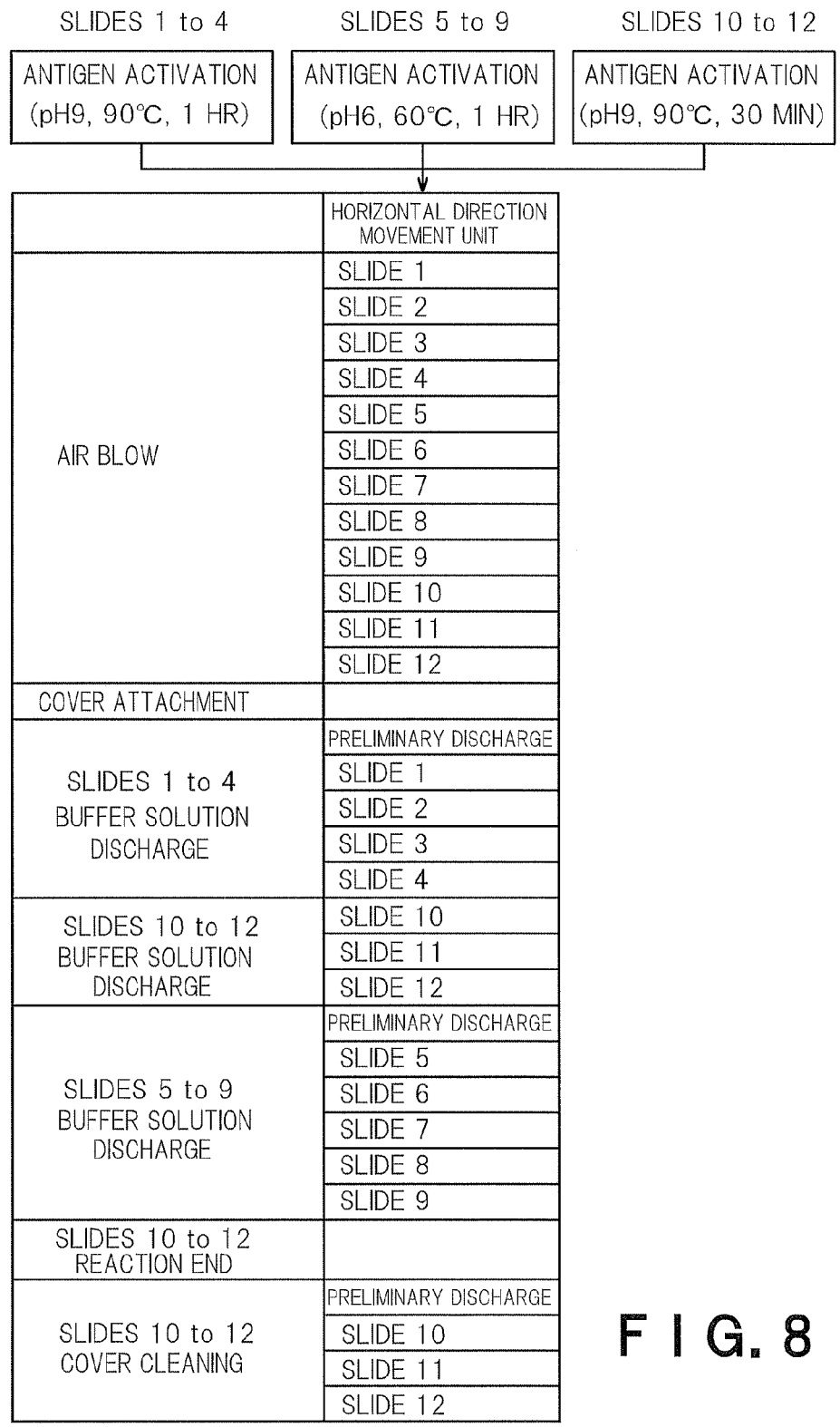
FIG. 8 is a diagram showing an example of a part of an integrated process sequence (a part corresponding to a part of an antigen retrieval treatment process by means of heating) generated by the automatic tissue staining device according to the embodiment of the present invention.

Since a sample from which the buffer solution has been blown off and removed is desired to be supplied with the treatment liquid in a short time, the integrated process sequence is generated so as to quickly supply a reagent or buffer solution to the sample after blowing off and removing the buffer solution from the sample. Therefore, the integrated process sequence is generated so that the processes from blowing gas such as air onto the glass slides 90 with the blow nozzles 75c and 75d to supplying the treatment liquids to the glass slides 90 are performed quickly in succession (see FIG. 8). In FIGS. 8, 9A and 9B, "AIR BLOW" represents the process of blowing gas such as air onto the glass slides 90 with the blow nozzles 75c and 75d.

Since a reagent remaining in/on the reagent needle 76 is undesirable, in cases where the reagent needle 76 is used in the setup process, the integrated process sequence is generated so that the processes from the suction of a reagent by the reagent needle 76 to the cleaning of the reagent needle are performed quickly in succession (see FIG. 9B).

In regard to the stoppage process, the integrated process sequence is generated so as to perform the processes from the preliminary discharge of a buffer solution or the like to the supply of the buffer solution from above the covers 25 quickly in succession in cases where the covers 25 are used, and to perform the processes from the preliminary discharge of a buffer solution or the like to the cleaning of the glass slides 90 quickly in succession in cases where no covers 25 are used.

Incidentally, the integrated process sequence is generated so that the order of cleaning the glass slides in the stoppage process is the same as the order in which the treatment liquid was supplied to the glass slides. However, since temperature rise speed or temperature fall speed can vary among the glass slides, the glass slides' time points when the time accumulation is started and the glass slides' time points when the temperature reaches the cover cleaning start temperature due to the cooling do not necessarily come in the aforementioned order. Further, the reaction time is set at the same length (1 hour) in the antigen retrieval treatment for the glass slides $90_1$ to $90_4$ and the antigen retrieval treatment for the glass slides $90_5$ to $90_9$ in FIG. 9A, and in such cases it is expected that the glass slides' time points when the time accumulation is started are close to each other and the glass slides' time points when the temperature reaches the cover cleaning start temperature due to the cooling are close to each other. Thus, there can be cases where the time to start a treatment on some of glass slides as targets of the antigen retrieval treatment to which a treatment liquid was supplied later comes before the arrival of the time to start a treatment on all glass slides as targets of the antigen retrieval treatment to which a treatment liquid was supplied earlier. In short, there are cases where the order in which the cleaning of glass slides should be started differs from the order of glass slides generated in the integrated process sequence. Therefore, the integrated process sequence is generated so that the reaction stoppage treatments for a plurality of glass slides whose specified reaction times are close to each other to some extent are performed quickly in succession (even if the specified conditions of the reaction treatments differ from each other).

[Selection of Glass Slides 90]

Incidentally, the control unit 50 to 55 in this embodiment compares the individual process sequence performed for each of the samples on glass slides 90 (the attribute of the inspection method) with each other and thereby judges whether or not the individual process sequences performed for samples belong to the same attribute, that is, have the same protocol. When the attribute of the individual process sequence performed for a certain sample and the attribute of the individual process sequence performed for another sample differ from each other, one or more glass slides 90 that should be removed from the holding unit 7 are specified so that individual process sequences of the same attribute are performed for samples on a plurality of glass slides 90 held in the holding unit 7 on a certain lane 6. Then, the operation monitoring device 40 makes a notification by displaying information indicating the glass slides 90 specified by the control unit 50 to 55 to be removed. Parenthetically, in this embodiment, the operation monitoring device 40 serves as the "notification unit" described in claims.

As above, in this embodiment, the operation monitoring device 40 guides the operator so that individual process sequences of the same attribute are performed for samples on glass slides 90 held in the holding unit 7 on a certain lane 6. Thus, samples to be treated with individual process sequences of the same attribute can be gathered on one lane 6 and an increase in the treatment efficiency can be expected. However, when there exists no other sample that can be treated at the time point, when the reduction in the treatment time cannot be expected even by moving the specified glass slides 90 to another lane 6, or the like, the operator may ignore the display on the operation monitoring device 40 and start the treatment while leaving the "specified glass slides 90" on the "certain lane 6."

It is also possible to employ the following mode: The control unit 50 to 55 may specify one or more glass slides 90 that should be removed from the holding unit 7 so that individual process sequences (inspection methods) of the same attribute are performed for the samples on all the glass slides 90 held in the holding unit 7 on each lane 6. Then, the operation monitoring device 40 may display (notify of) another lane 6 (one of the remaining two lanes 6) on which the glass slides 90 specified to be removed should be set. The "another lane 6" specified in this case is, for example, a lane 6 on which individual process sequences of the same attribute as the samples on the glass slides 90 specified to be removed are scheduled to be performed.

When such a mode is employed, it is possible to notify the operator of on which lane 6 the removed glass slides 90 should be set, and the operator can move the removed glass slides 90 to an appropriate lane 6 without the need of wavering at all.

Even in this mode, when there exists no other lane 6 on which the glass slides 90 specified to be removed should be set, the operation monitoring device 40 may simply display information indicating that the glass slides 90 specified to be removed are removed from the lane 6, without displaying the "another lane 6" on which the specified glass slides 90 should be set.

[Setting of New Glass Slides 90]

Figure 12:
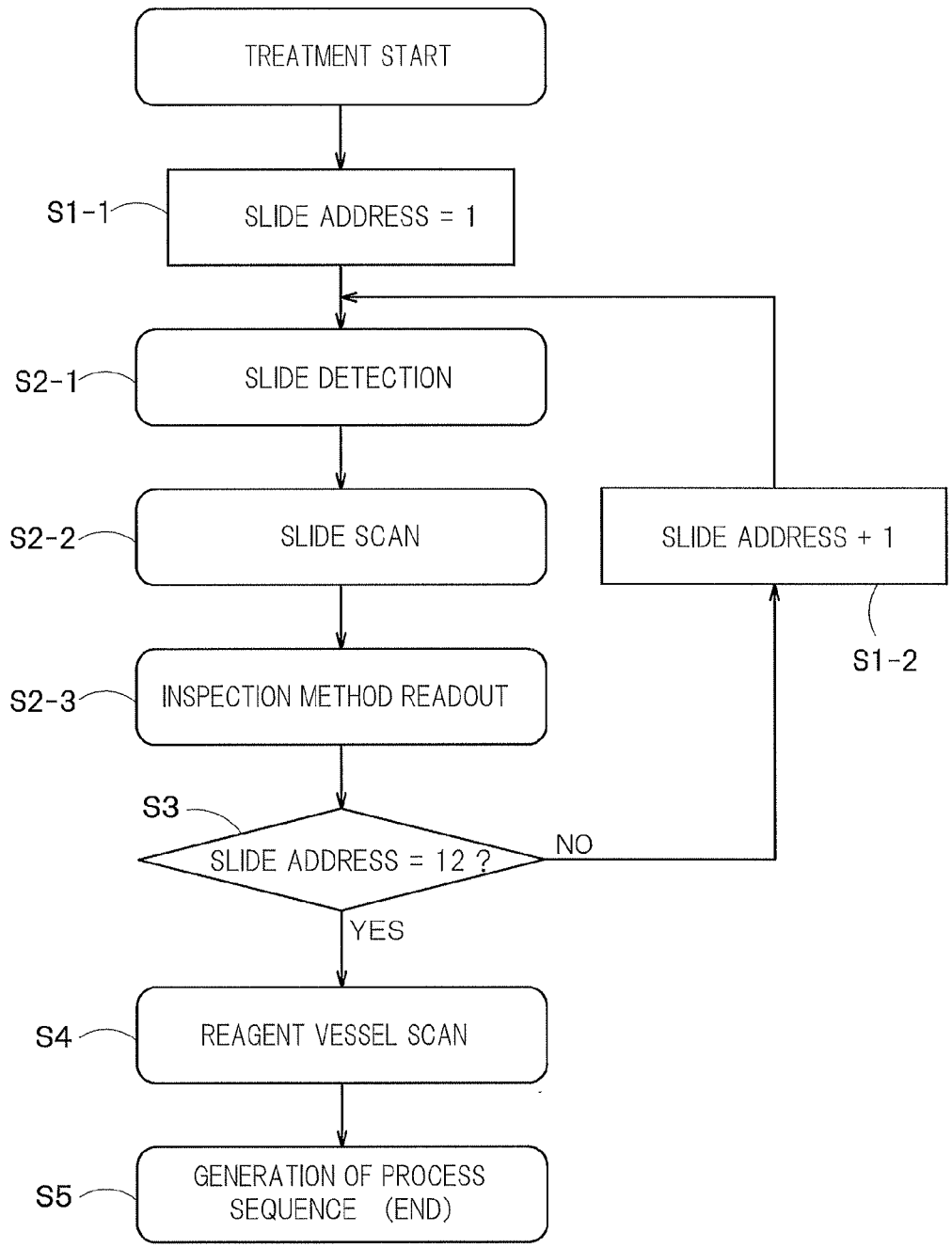
FIG. 12 is a flow chart for explaining a treatment performed when new glass slides are set on a lane in the automatic tissue staining device according to the embodiment of the present invention.

Next, a treatment performed when new glass slides 90 are set on a lane 6 will be described below by mainly referring to FIG. 12.

After an operation for accepting a holding unit 7 holding new glass slides 90 is performed on the operation unit 43 of the operation monitoring device 40, if the targeted lane 6 has the highest priority as the result of judging whether the horizontal direction movement unit 10 is usable or not based on the aforementioned priority rules and comparing the suspension times, etc., the horizontal direction movement unit 10 is moved to the position (hereinafter referred to as an "address") of each glass slide 90 that can be held on the lane 6 and the following treatment is started for each glass slide 90 successively from an address at the deepest position in the lane 6.

First, an address at which the treatment should be performed is checked by the ultrasonic sensor 77 (see FIG. 6) attached to the horizontal direction movement unit 10. If a glass slide 90 set at the address is detected, the address is registered in the glass slide position management register master 86 (see S2-1). Incidentally, the address of the first glass slide 90 has been set at "1" (see S1-1).

Subsequently, in the case where a glass slide 90 has been set at the address, the two-dimensional bar code affixed on the glass slide 90 is scanned by the scanning sensor 78 (see FIG. 6) attached to the horizontal direction movement unit 10 and the scanned information is registered in the glass slide position management register master 86 while associating the information with the address (see S2-2).

Subsequently, the inspection procedure database 81 is referred to based on the "inspection method code" included in the information, information on the operation procedure of the corresponding inspection method and necessary reagents is acquired, and the acquired information is stored in the glass slide position management register master 86 while associating the information with the address (see S2-3).

Subsequently, whether the address of the glass slide 90 has reached the number of glass slides 90 that can be held on the lane 6 ("12" in this embodiment) or not is judged (see S3). If the address of the glass slide 90 has not reached the number of glass slides 90 that can be held on the lane 6, the address of the glass slide 90 is incremented by "1," the horizontal direction movement unit 10 moves to the next address on the lane 6, and the aforementioned steps S2-1 to S2-3 are performed successively.

In contrast, if the address of the glass slide 90 has reached the number of glass slides 90 that can be held on the lane 6, reagent vessels 91 on the reagent vessel stand 4 are successively checked by the ultrasonic sensor 77 and the scanning sensor 78 attached to the horizontal direction movement unit 10 and the presence/absence of a reagent vessel 91 scheduled to be used is detected. If a reagent vessel 91 scheduled to be used exists on the reagent vessel stand 4, the open-close status of the reagent vessel 91 is checked. If the cover of the reagent vessel 91 is open, the remaining amount of the reagent in the reagent vessel 91 is measured (see S4). In contrast, if the cover of the reagent vessel 91 scheduled to be used is closed or the remaining amount of the reagent to be used is insufficient, the display unit 42 of the operation monitoring device 40 notifies of an error.

Subsequently, all treatments for all the glass slides 90 situated on the lane 6 are reconfigured as a sequence of execution procedures of the horizontal direction movement unit 10, the integrated process sequence is generated based on the execution procedures, and the generated integrated process sequence is stored in the process sequence register master 87 (see S5). In this case, as mentioned earlier, the operation monitoring device 40 guides the operator based on the information stored in the glass slide position management register master 86 so that individual process sequences of the same attribute are performed for samples on glass slides 90 held in the holding unit 7 on the lane 6. Incidentally, at the point when the removal of the holding unit 7 from the lane 6 is detected, the integrated process sequence of the lane 6 is discarded from the register master.

<<Automatic Tissue Staining Method and Effect>>

Next, an automatic tissue staining method using the automatic tissue staining device 100 configured as above and effects achieved by the automatic tissue staining device 100 and the automatic tissue staining method, not mentioned yet or especially important, will be explained below.

In the automatic tissue staining device 100 of this embodiment, the control unit 50 to 55 judges the occupancy status of the horizontal direction movement unit 10 prior to supplying an organic solvent from the organic solvent nozzle 75b to the samples on the glass slides 90 held in the holding unit 7 on a certain lane 6 (i.e., the first samples), supplying a buffer solution from the buffer solution nozzle 75a to the first samples, or blowing gas from the blow nozzles 75c and 75d onto the first samples. In this case, the treatment for the first samples is suspended if the horizontal direction movement unit 10 is occupied. Incidentally, such a judgment is made every $1/100$ seconds, for example.

Further, in this embodiment, the computation unit 44 starts the time count and performs the time accumulation from the time point when the sample is judged to have reached a prescribed temperature at the temperature measurement unit 21, and the occupancy status of the horizontal direction movement unit 10 is judged in real time. Therefore, more precise reaction time (treatment time) can be secured. This point will be explained below. In this embodiment, the computation unit 44 starts the time count and performs the time accumulation from the time point when the sample is judged to have reached the prescribed temperature at the temperature measurement unit 21. In this regard, the temperature rise speed or the temperature fall speed of the heating unit 20 can vary for various reasons; however, it is possible in this embodiment to accumulate the reaction time or the like securely after the sample has reached the prescribed temperature because the computation unit 44 starts the time count and performs the time accumulation from the time point when the sample is judged to have reached the prescribed temperature at the temperature measurement unit 21 as mentioned above.

On the other hand, if the time accumulation is started after the sample reaches the prescribed temperature as above, the occupancy status of the horizontal direction movement unit 10 can deviate from the schedule provisionally calculated by using the standard treatment times. In this regard, in modes in which the horizontal direction movement unit 10 is used exactly according to a preset schedule as in the conventional technology, each treatment is performed exactly according to the preset schedule even if a prescribed time has not elapsed since the prescribed temperature is reached or even if the elapsed time since the prescribed temperature is reached has exceeded the prescribed time. Consequently, carrying out the treatments according to precise treatment times is difficult in conventional modes like the method disclosed in U.S. Pat. No. 8,315,899. In contrast, in this embodiment, the treatments using the horizontal direction movement unit 10 are performed not exactly according to a preset schedule but based on the actual temperatures measured by the temperature measurement units 21. Further, since no usage schedule of the horizontal direction movement unit is preset as a schedule in this embodiment, the control unit 50 to 55 judges the occupancy status of the horizontal direction movement unit 10 every $1/100$ seconds, for example, prior to the supply of a treatment fluid from the supply head 11 to the first samples. If the horizontal direction movement unit 10 is occupied at that stage, the start of the treatment for the first samples is suspended. If the horizontal direction movement unit 10 is not occupied, the treatment for the first samples is permitted. Therefore, treatments can be carried out mostly according to precise treatment times while grasping the usage status of the horizontal direction movement unit 10 in real time.

Further, in this embodiment, even when the horizontal direction movement unit 10 is not occupied at the present stage as the result of judging the present occupancy status of the horizontal direction movement unit 10 prior to the supply of a treatment fluid from the supply head 11 to the first samples, a comparison is made between the usage schedule of the horizontal direction movement unit 10 in the treatment for the first samples and the usage schedule of the horizontal direction movement unit 10 in the treatment for second samples (e.g., the "reaction stoppage-scheduled second samples") on the two lanes 6 other than the aforementioned "certain lane" and a judgment is made on whether or not there is an overlap between the times of using the horizontal direction movement unit 10 in the treatment for the first samples and the times of using the horizontal direction movement unit 10 in the treatment for the second samples. More specifically, a comparison is made between the usage schedule of the horizontal direction movement unit 10 in the treatment for a plurality of first samples situated on a certain lane 6 and the usage schedule of the horizontal direction movement unit 10 in the treatment for a plurality of second samples situated on another lane 6 by comparing treatment schedules after the present time in the integrated process sequences.

Incidentally, since there are three lanes in this embodiment, the times in which the horizontal direction movement unit 10 is scheduled to be used in the treatment for the second samples are calculated by using both of the integrated process sequence for a plurality of samples situated on one (e.g., the lane 6 at the center in FIG. 2) of the lanes 6 other than the certain lane 6 (e.g., the lane 6 on the right-hand side in FIG. 2) and the integrated process sequence for a plurality of samples situated on the remaining one (e.g., the lane 6 on the left-hand side in FIG. 2) of the lanes 6 other than the certain lane 6.

When the treatment for the first samples can be started and the treatment for the second samples cannot be started and there is no overlap between the usage schedule of the horizontal direction movement unit 10 in the case where the treatment for a plurality of first samples situated on the certain lane 6 is started and the usage schedule of the horizontal direction movement unit 10 in the treatment for a plurality of second samples situated on another lane 6 as the result of comparing those usage schedules by comparing treatment schedules after the present time in the integrated process sequences, the treatment for the plurality of first samples situated on the certain lane 6 is permitted.

In contrast, when the treatment for the first samples can be started and (1) the treatment for the second samples can be started or (2) the treatment for the second samples cannot be started and there is an overlap between the usage schedule of the horizontal direction movement unit 10 (the times of using the horizontal direction movement unit 10) in the case where the treatment for a plurality of first samples situated on the certain lane 6 is started and the usage schedule of the horizontal direction movement unit 10 (the times of using the horizontal direction movement unit 10) in the treatment for a plurality of second samples situated on another lane 6 as the result of comparing those usage schedules by comparing treatment schedules after the present time in the integrated process sequences, the control unit 50 to 55 judges whether or not the contents of the treatment schedule for the plurality of first samples situated on the certain lane 6 and having such an overlapping treatment schedule have priority over the contents of the treatment schedule for the plurality of second samples situated on the other lane 6 and having such an overlapping treatment schedule.

Then, if the contents of the treatment schedule for the plurality of first samples situated on the certain lane 6 and having the overlapping treatment schedule have priority over the contents of the treatment schedule for the plurality of second samples situated on the other lane 6 and having the overlapping treatment schedule, the start of the soonest treatment for the first samples using the horizontal direction movement unit 10 is permitted and the soonest treatment is started. In contrast, if the contents of the treatment schedule for the plurality of second samples situated on the other lane 6 and having the overlapping treatment schedule have priority over the contents of the treatment schedule for the plurality of first samples situated on the certain lane 6 and having the overlapping treatment schedule, the start of the soonest treatment for the first samples using the horizontal direction movement unit 10 is suspended.

The method of determining the priorities is as already explained above. Effects obtained by employing the priorities will be explained below.

In this embodiment, when the contents of the treatment schedule for the first samples are a treatment of "stopping the reaction" upon the first samples and the contents of the treatment schedule for the second samples are a treatment other than a treatment of "stopping the reaction" upon the second samples, the contents of the treatment schedule for the first samples are prioritized over the contents of the treatment schedule for the second samples. Therefore, the reaction stoppage treatment can be conducted with high priority and deterioration in the inspection accuracy caused by progress of the reaction for an excessive time can be prevented.

Further, in this embodiment, when the contents of the treatment schedules for the first samples and the second samples are treatments other than treatments of stopping the reactions upon the first samples and the second samples and the time for which the soonest treatment to be performed for the first samples by using the horizontal direction movement unit 10 has been suspended is longer than the time for which the soonest treatment to be performed for the second samples by using the horizontal direction movement unit 10 has been suspended, the contents of the (soonest) treatment schedule for the first samples are prioritized over the contents of the (soonest) treatment schedule for the second samples. Therefore, the treatment for the first samples can be prevented from remaining suspended for a long time.

Furthermore, in this embodiment, when the contents of the treatment schedule for the first samples are a treatment of stopping the reaction upon the first samples and the contents of the treatment schedule for the second samples are also a treatment of stopping the reaction upon the second samples, the contents of the treatment schedule for the first samples are prioritized over the contents of the treatment schedule for the second samples if the contents of the treatment schedule for the first samples are a treatment of "stopping a reaction of a primary antibody" upon an antigen in the first sample and the contents of the treatment schedule for the second samples are a treatment other than a treatment of "stopping a reaction of a primary antibody" upon an antigen in the second sample. Therefore, the treatment of stopping the reaction of the primary antibody can be conducted with high priority and a drop in the inspection accuracy caused by excessive progress of the reaction of the primary antibody, which is especially sensitive to the length of the reaction time, can be prevented.

Moreover, in this embodiment, when the contents of the treatment schedule for the first samples are a treatment of stopping the reaction upon the first samples and the contents of the treatment schedule for the second samples are also a treatment of stopping the reaction upon the second samples, the contents of the treatment schedule for the first samples are prioritized over the contents of the treatment schedule for the second samples if the "reaction time" for the first samples being stoppage targets is shorter than the "reaction time" for the second samples being stoppage targets. In cases where the reaction time specified by a detection system or a staining program is short, if the reaction is extended, the influence of the extension of the reaction time tends to be significant. In this embodiment, a reaction whose original reaction time is short can mostly be prevented from progressing excessively, and consequently, a drop in the inspection accuracy can be prevented.

Parenthetically, in this embodiment, the check valves 74a to 74g are provided at the discharge-side ends of the guide pipes 71a to 71g extending respectively from the reservoir units 70a to 70g as shown in FIG. 7. Further, the mixing of different buffer solutions or organic solvents can be confined to regions from the discharge-side ends of the guide pipes 71a to 71g to the discharge outlets of the liquid supply nozzles 75a and 75b. Thus, the amount of the aforementioned "preliminary discharge" can be reduced, and consequently, the time necessary for the "preliminary discharge" can be shortened significantly. Accordingly, it is possible to mostly prevent the occupancy status of the horizontal direction movement unit 10 from deviating from the originally planned schedule.

Figure 13:
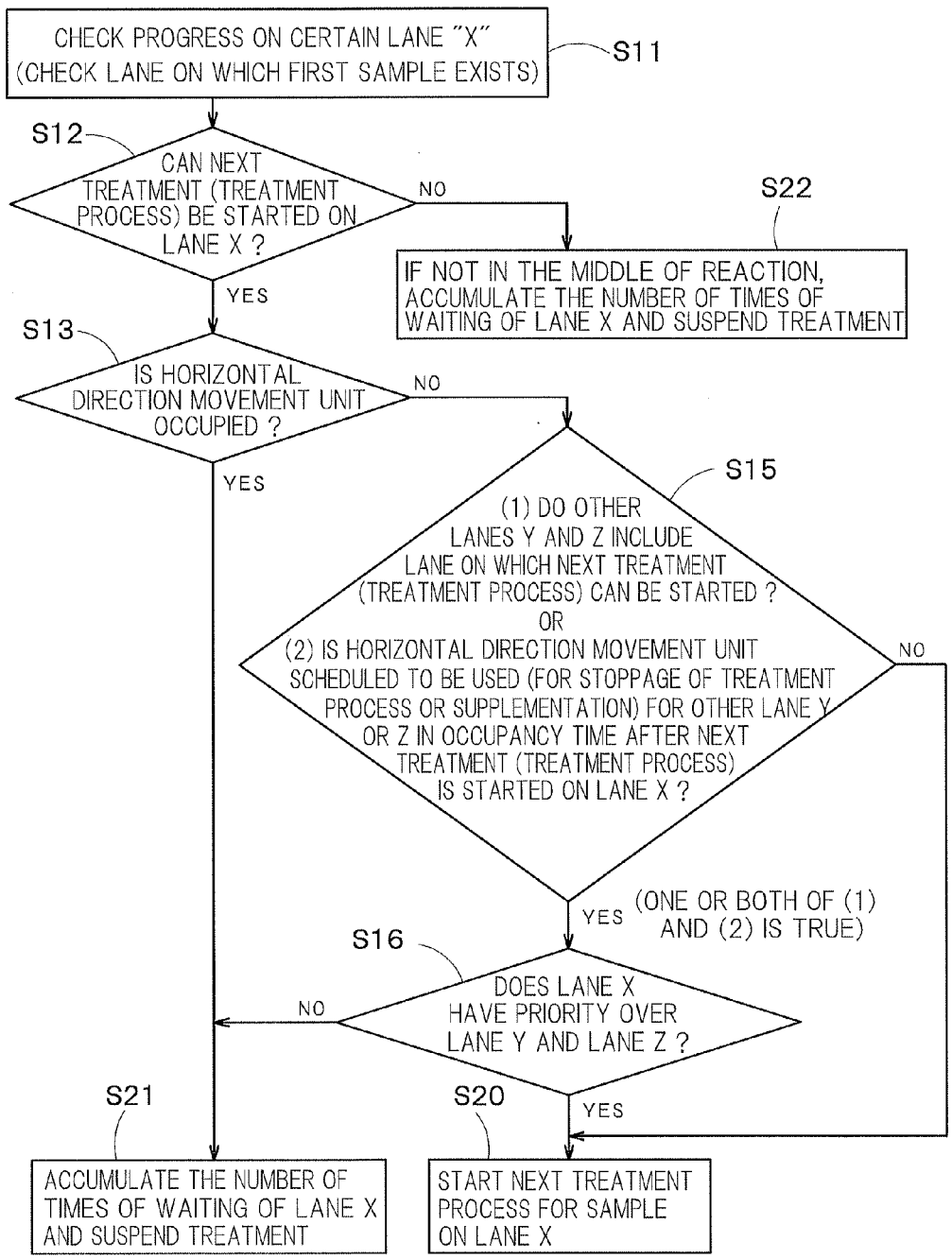
FIG. 13 is a flow chart for explaining an automatic tissue staining method using the automatic tissue staining device according to the embodiment of the present invention.

FIG. 13 illustrates an example of the flow of the automatic tissue staining method using the above-described automatic tissue staining device.

First, the control unit 50 to 55 checks the progress on a certain lane X (see S11). The control unit 50 to 55 judges whether the next treatment can be started on the lane X (see S12). In this embodiment, steps from S11 in FIG. 13 are successively performed for each of three lanes 6, for example. When it is judged that the treatment can be started on a lane 6, that is, when S16 in FIG. 13 is YES, the check (S11) regarding the other lanes 6 is stopped. In contrast, when the judgment is made to suspend the treatment on the checked lane 6 (S21 or S22), the steps from S11 in FIG. 13 are continued for the other lanes 6 unless the judgment that the treatment can be started on a lane 6 is made.

When a reaction or the like on the lane X has not finished and the next treatment using the horizontal direction movement unit 10 cannot be started, the computation unit 44 accumulates the number of times of waiting (waiting time) of the lane X (only when a treatment or reaction on the lane X has not been started) and the control unit 50 to 55 suspends the treatment on the lane X (see S22). In contrast, when the reaction or the like on the lane X has finished and the next treatment using the horizontal direction movement unit 10 can be started, the control unit 50 to 55 checks whether or not the horizontal direction movement unit 10 is occupied at that time point (see S13). Incidentally, if a treatment is in progress on one of the lanes 6, the horizontal direction movement unit 10 is regarded to be occupied and the start of a treatment is suspended on all the lanes 6. Therefore, the flow shown in FIG. 13 may be changed so that S13 is executed as the step next to S11 and the process advances to the step S12 when the judgment in S13 is YES.

If the horizontal direction movement unit 10 is occupied at that time point, the computation unit 44 accumulates the number of times of waiting (waiting time) of the lane X and the control unit 50 to 55 suspends the treatment on the lane X (see S21). In contrast, if the horizontal direction movement unit 10 is not occupied at that time point, the control unit 50 to 55 checks whether or not the other lanes Y and Z include a lane on which the next treatment can be started, or whether or not the horizontal direction movement unit 10 is scheduled to be used (for the stoppage of a treatment process or the supplementation) for reaction stoppage-scheduled second samples on one of the remaining two lanes Y and Z in an occupancy time after the next treatment using the horizontal direction movement unit 10 is started on the lane X (see S15).

If the control unit 50 to 55 judges that the other lanes Y and Z include no lane on which the next treatment can be started and the horizontal direction movement unit 10 is not scheduled to be used (for the stoppage of a treatment process or the supplementation) for second samples (e.g., "reaction stoppage-scheduled second samples") on one of the remaining two lanes Y and Z in the occupancy time after the next treatment using the horizontal direction movement unit 10 is started on the lane X, the next treatment using the horizontal direction movement unit 10 for the samples on the lane X is started (see S20). In contrast, if the control unit 50 to 55 judges that the other lanes Y and Z include a lane on which the next treatment can be started in the occupancy time after the next treatment using the horizontal direction movement unit 10 is started on the lane X or the horizontal direction movement unit 10 is scheduled to be used (for the stoppage of a treatment process or the supplementation) for second samples on one of the remaining two lanes Y and Z in the occupancy time after the next treatment using the horizontal direction movement unit 10 is started on the lane X, the control unit 50 to 55 judges whether or not the treatment using the horizontal direction movement unit 10 for the lane X has priority over the treatment using the horizontal direction movement unit 10 for the lane Y and the treatment using the horizontal direction movement unit 10 for the lane Z (see S16).

If the control unit 50 to 55 judges that the treatment using the horizontal direction movement unit 10 for the lane X has priority over the treatment using the horizontal direction movement unit 10 for the lane Y and the treatment using the horizontal direction movement unit 10 for the lane Z, the next treatment using the horizontal direction movement unit 10 for the samples on the lane X is started (see S20). In contrast, if the control unit 50 to 55 judges that the treatment using the horizontal direction movement unit 10 for the lane X does not have priority over the treatment using the horizontal direction movement unit 10 for the lane Y and the treatment using the horizontal direction movement unit 10 for the lane Z, the computation unit 44 accumulates the number of times of waiting (waiting time) of the lane X and the control unit 50 to 55 suspends the treatment on the lane X (see S21).

Incidentally, these priorities are as already explained earlier.

When all the lanes 6 resulted in suspending the treatment (S21 or S22), the next treatment is not started for any lane 6 as a result. This also includes the following case, for example: When a treatment is in progress on a certain lane 6, the horizontal direction movement unit 10 is regarded to be occupied, and thus the certain lane 6 is regarded to be in the state of S22 in FIG. 13 and the other lanes 6 are regarded to be in the state of S21 in FIG. 13 according to the flow shown in FIG. 13.

Even when the process resulted in not starting the next treatment as above or in starting the next treatment on a lane 6, the flow of FIG. 13 is carried out in the same way as the above explanation ¹⁄₁₀₀ seconds after the start of the flow of FIG. 13, for example, and thereafter the iteration is continued. By performing the check at short periods and determining the lane 6 to start the next treatment (or determining not to start the next treatment on any lane 6) as above, the end of the occupancy of the horizontal direction movement unit 10 can be detected substantially in real time and the treatment on the most appropriate lane 6 at that time point can be started. Thus, even when a deviation from the schedule provisionally calculated from the standard times has occurred, treatments can be carried out for samples on each lane 6 appropriately based on the previously specified inspection methods.

Further, since the judgment in S13 in FIG. 13 remains YES for all the lanes 6 and the start of another treatment is suspended until the treatment already started on a lane 6 ends, the sequence of execution procedures of the horizontal direction movement unit 10 for all the glass slides 90 situated on the lane 6 undergoing the already started treatment, reconfigured in regard to processes aggregated to some extent at the time of generating the integrated process sequence, can be carried out quickly in succession.

Incidentally, while the explanation of the above example has been given of an automatic tissue staining device 100 including a control unit 50 to 55 that compares the individual process sequences, each including a plurality of treatment processes performed for a corresponding one of samples on a plurality of glass slides 90, with each other and controls the treatment processes for the samples based on the integrated process sequence generated so as to consecutively perform treatment processes of the same contents on the samples, it is not necessarily essential to perfectly generate the integrated process sequence for the samples. Specifically, the automatic tissue staining device 100 may include a control unit 50 to 55 that compares the individual process sequences of the samples (each individual process sequence including a plurality of treatment processes performed for a sample) with each other while limiting the comparison to treatment processes in a specified range after the present time and executes control so as to consecutively perform treatment processes of the same contents on the samples.

In that case, the automatic tissue staining device 100 may include a control unit 50 to 55 that performs control as follows, for example: When one or more glass slides 90 are situated in a first region and one or more glass slides 90 are situated in a second region different from the first region, the control unit 50 to 55 makes a comparison between the usage schedule of the horizontal direction movement unit 10 in a treatment for first samples on the one or more glass slides 90 situated in the first region and the usage schedule of the horizontal direction movement unit 10 in a treatment for second samples on the one or more glass slides 90 situated in the second region and thereby judges whether or not there is an overlap between the times of using the horizontal direction movement unit 10 in the treatment for the first samples and the times of using the horizontal direction movement unit 10 in the treatment for the second samples. When there is an overlap between the times of using the horizontal direction movement unit 10 in the treatment for the first samples and the times of using the horizontal direction movement unit 10 in the treatment for the second samples, the control unit 50 to 55 makes a comparison between the contents of the treatment schedule for the first samples and the contents of the treatment schedule for the second samples in the overlapping time. When the contents of the treatment schedule for the first samples have priority over the contents of the treatment schedule for the second samples, the control unit 50 to 55 may permit the start of the soonest treatment for the first samples using the horizontal direction movement unit 10. When the contents of the treatment schedule for the second samples have priority over the contents of the treatment schedule for the first samples, the control unit 50 to 55 may suspend the start of the soonest treatment for the first samples using the horizontal direction movement unit 10.

Further, in that case, the automatic tissue staining device 100 may include a control unit 50 to 55 that performs control as follows, for example: The control unit 50 to 55 judges whether or not the soonest treatment for second samples on one or more glass slides 90 situated in a second region can be started. When the soonest treatment for the second samples can be started, the control unit 50 to 55 makes a comparison between the contents of the treatment schedule for first samples on one or more glass slides 90 situated on a first region and the contents of the treatment schedule for the second samples. When the contents of the treatment schedule for the first samples have priority over the contents of the treatment schedule for the second samples, the control unit 50 to 55 may permit the start of the soonest treatment for the first samples using the horizontal direction movement unit 10. When the contents of the treatment schedule for the second samples have priority over the contents of the treatment schedule for the first samples, the control unit 50 to 55 may suspend the start of the soonest treatment for the first samples using the horizontal direction movement unit 10.

Incidentally, each of the above-described components and functions can be properly implemented by an arbitrary type of hardware, software or combination of hardware and software. Further, the present invention is applicable also to a program for causing a computer to execute the above-described treatment steps (treatment procedures), a computer-readable record medium (nontemporary record medium) storing such a program, and a device such as a computer in which such a program can be installed, for example.

Lastly, the disclosure of the description and drawings of the above embodiment is just an example for specifically explaining the inventions described in the claims, and thus the inventions described in the claims are not restricted by the disclosure of the description and drawings of the above embodiment.

DESCRIPTION OF REFERENCE CHARACTERS

6: Lane
7: Holding unit
10: Horizontal direction movement unit
11: Supply head
20: Heating unit
21: Temperature measurement unit
44: Computation unit (accumulation unit)
90: Glass slide
70*a* to 70*g*: Reservoir unit
71*a* to 71*g*: Guide pipe
72*a* to 72*g*: Liquid sending unit
74*a* to 74*g*: Check valve
75*a* to 75*d*: Nozzle
100: Automatic tissue staining device

The invention claimed is:

1. An automatic tissue staining device comprising:
a supply head configured to supply a treatment fluid;
a horizontal direction movement unit configured to move the supply head in a horizontal direction;
a holding unit configured to hold a plurality of glass slides on which samples are set, the holding unit including a first region and a second region different from the first region; and
a control unit configured to judge an occupancy status of the horizontal direction movement unit in a condition that one or more of the glass slides are situated in the first region, prior to supply of the treatment fluid from the supply head to one or more samples on the one or more glass slides situated in the first region; suspend a start of a soonest treatment for the one or more samples on the one or more glass slides situated in the first region when the horizontal direction movement unit is occupied; and permit the start of the soonest treatment for the one or more samples on the one or more glass slides situated in the first region when the horizontal direction movement unit is not occupied.

2. The automatic tissue staining device according to claim 1, further comprising:
a heating unit for heating the samples on the plurality of glass slides;
a temperature measurement unit for measuring a temperature of the samples heated by the heating unit; and
an accumulation unit configured to judge that the temperature of the samples has reached a prescribed temperature according to a result of measurement by the temperature measurement unit, start a count, and perform accumulation,
wherein:
the treatment fluid includes a treatment liquid, and
the accumulation unit is configured to start the count when the samples on the plurality of glass slides are supplemented with the treatment liquid and restart the count when the prescribed temperature is reached after supplementation with the treatment liquid.

3. The automatic tissue staining device according to claim 2, wherein:
one or more of the glass slides are situated in the second region,
the control unit is configured to make a comparison between a usage schedule of the horizontal direction movement unit in a case where a treatment for one or more first samples on the one or more glass slides situated in the first region is started and a usage schedule of the horizontal direction movement unit in a treatment for one or more second samples on the one or more glass slides situated in the second region, and thereby judge whether or not there is an overlap between a time of using the horizontal direction movement unit in the case where the treatment for the one or more first samples is started and a time of using the horizontal direction movement unit in the treatment for the one or more second samples,
when there is an overlap between the time of using the horizontal direction movement unit in the case where the treatment for the one or more first samples is started and the time of using the horizontal direction movement unit in the treatment for the one or more second samples, the control unit is configured to make a comparison between contents of a treatment schedule for the one or more first samples and contents of a treatment schedule for the one or more second samples in the overlapping time,
when the contents of the treatment schedule for the one or more first samples have priority over the contents of the treatment schedule for the one or more second samples, the control unit is configured to permit the start of the soonest treatment for the one or more first samples using the horizontal direction movement unit, and
when the contents of the treatment schedule for the one or more second samples have priority over the contents of the treatment schedule for the one or more first samples, the control unit is configured to suspend the start of the soonest treatment for the one or more first samples using the horizontal direction movement unit.

4. The automatic tissue staining device according to claim 3, wherein when the contents of the treatment schedule for the one or more first samples are a treatment of stopping a reaction upon the one or more first samples and the contents of the treatment schedule for the one or more second samples are a treatment other than a treatment of stopping a reaction upon the one or more second samples, the contents of the treatment schedule for the one or more first samples are prioritized over the contents of the treatment schedule for the one or more second samples.

5. The automatic tissue staining device according to claim 4, wherein when the contents of the treatment schedule for the one or more first samples are a treatment other than a treatment of stopping a reaction upon the one or more first samples and the contents of the treatment schedule for the one or more second samples are a treatment other than a treatment of stopping a reaction upon the one or more second samples and a time for which the soonest treatment to be performed for the one or more first samples by using the horizontal direction movement unit has been suspended is longer than a time for which the soonest treatment to be performed for the one or more second samples by using the horizontal direction movement unit has been suspended, the contents of the treatment schedule for the one or more first samples are prioritized over the contents of the treatment schedule for the one or more second samples.

6. The automatic tissue staining device according to claim 5, wherein when the contents of the treatment schedule for the one or more first samples are a treatment of stopping the reaction upon the one or more first samples and the contents of the treatment schedule for the one or more second samples are a treatment of stopping the reaction upon the one or more second samples, the contents of the treatment schedule for the one or more first samples are prioritized over the contents of the treatment schedule for the one or more second samples if a reaction time specified for the one or more first samples being stoppage targets is shorter than a reaction time specified for the one or more second samples being stoppage targets.

7. The automatic tissue staining device according to claim 6, wherein when the one or more first samples and the one or more second samples are samples for which an immunostaining method has been specified as a staining method and the contents of the treatment schedule for the one or more first samples are a treatment of stopping the reaction upon the one or more first samples and the contents of the treatment schedule for the one or more second samples are a treatment of stopping the reaction upon the one or more second samples, the contents of the treatment schedule for the one or more first samples are prioritized over the contents of the treatment schedule for the one or more second samples if the contents of the treatment schedule for the one or more first samples are a treatment of stopping a reaction of a primary antibody upon an antigen in the one or more first samples and the contents of the treatment schedule for the one or more second samples are a treatment other than a treatment of stopping a reaction of a primary antibody upon an antigen in the one or more second samples.

8. The automatic tissue staining device according to claim 3, wherein when the contents of the treatment schedule for the one or more first samples are a treatment other than a treatment of stopping a reaction upon the one or more first samples and the contents of the treatment schedule for the one or more second samples are a treatment other than a treatment of stopping a reaction upon the one or more second samples and a time for which the soonest treatment to be performed for the one or more first samples by using the horizontal direction movement unit has been suspended is longer than a time for which the soonest treatment to be performed for the one or more second samples by using the horizontal direction movement unit has been suspended, the contents of the treatment schedule for the one or more first samples are prioritized over the contents of the treatment schedule for the one or more second samples.

9. The automatic tissue staining device according to claim 8, wherein when the contents of the treatment schedule for the one or more first samples are a treatment of stopping the reaction upon the one or more first samples and the contents of the treatment schedule for the one or more second samples are a treatment of stopping the reaction upon the one or more second samples, the contents of the treatment schedule for the one or more first samples are prioritized over the contents of the treatment schedule for the one or more second samples if a reaction time specified for the one or more first samples being stoppage targets is shorter than a reaction time specified for the one or more second samples being stoppage targets.

10. The automatic tissue staining device according to claim 8, wherein when the one or more first samples and the one or more second samples are samples for which an immunostaining method has been specified as a staining method and the contents of the treatment schedule for the one or more first samples are a treatment of stopping the reaction upon the one or more first samples and the contents of the treatment schedule for the one or more second samples are a treatment of stopping the reaction upon the one or more second samples, the contents of the treatment schedule for the one or more first samples are prioritized over the contents of the treatment schedule for the one or more second samples if the contents of the treatment schedule for the one or more first samples are a treatment of stopping a reaction of a primary antibody upon an antigen in the one or more first samples and the contents of the treatment schedule for the one or more second samples are a treatment other than a treatment of stopping a reaction of a primary antibody upon an antigen in the one or more second samples.

11. The automatic tissue staining device according to claim 3, wherein when the treatment for the one or more second samples cannot be started and there is no overlap between a time of using the horizontal direction movement unit in the treatment schedule for the one or more first samples and a time of using the horizontal direction movement unit in the treatment schedule for the one or more second samples, the control unit is configured to permit the treatment for the one or more first samples.

12. The automatic tissue staining device according to claim 3, further comprising a plurality of lanes, wherein:
the same number of holding units as lanes is provided,
the lanes are provided respectively with the holding units,
a certain one of the lanes corresponds to the first region, and
another lane different from the certain one of the lanes corresponding to the first region corresponds to the second region.

13. The automatic tissue staining device according to claim 3, wherein the control unit is configured to compare treatment schedules from a present time in integrated process sequences generated for a plurality of regions, respectively, to each include a sequence of treatment processes for a plurality of samples in each of the plurality of regions with each other, thereby make a comparison between a usage schedule of the horizontal direction movement unit in a case where a treatment for a plurality of first samples situated in a certain region in the plurality of regions is started and a usage schedule of the horizontal direction movement unit in a treatment for a plurality of second samples situated in another region, and thereby judge whether or not there is an overlap between the time of using the horizontal direction movement unit in the case where the treatment for the plurality of first samples is started and the time of using the horizontal direction movement unit in the treatment for the plurality of second samples.

14. The automatic tissue staining device according to claim 13, wherein the integrated process sequences are generated by comparing individual process sequences, each including a plurality of treatment processes performed for the plurality of samples, respectively, with each other in each of the plurality of regions so as to consecutively perform treatment processes of the same contents on a plurality of samples on each of the plurality of regions.

15. The automatic tissue staining device according to claim 14, wherein the integrated process sequences are generated by comparing contents of treatment liquids included in the treatment fluids supplied to the respective samples in the consecutively performed treatment processes of the same contents so that samples using the same treatment liquid are consecutively supplied with the same treatment liquid.

16. The automatic tissue staining device according to claim 15, wherein the integrated process sequences are generated so as to supply the treatment liquid included in the treatment fluid to a sample whose reaction time is longer prior to a sample whose reaction time is shorter in the consecutively performed treatment processes of the same contents.

17. The automatic tissue staining device according to claim 14, wherein the integrated process sequences are generated so as to supply the treatment liquid included in the treatment fluid to a sample whose reaction time is longer prior to a sample whose reaction time is shorter in the consecutively performed treatment processes of the same contents.

18. The automatic tissue staining device according to claim 14, further comprising:
a heating unit for heating the samples on the plurality of glass slides; and
a temperature measurement unit for measuring a temperature of the samples heated by the heating unit,
wherein the integrated process sequences are generated so as to supply a treatment liquid included in the treatment fluid to a sample whose reaction temperature is higher prior to a sample whose reaction temperature is lower in the consecutively performed treatment processes of the same contents.

19. The automatic tissue staining device according to claim 3, wherein:
the control unit is configured to judge whether or not a soonest treatment for one or more second samples on the one or more glass slides situated in the second region can be started,
when the soonest treatment for the one or more second samples can be started, the control unit is configured to make a comparison between contents of a soonest treatment schedule for one or more first samples on the one or more glass slides situated in the first region and contents of a soonest treatment schedule for the one or more second samples,
when the contents of the soonest treatment schedule for the one or more first samples have priority over the contents of the soonest treatment schedule for the one or more second samples, the control unit is configured to permit the start of the soonest treatment for the one or more first samples using the horizontal direction movement unit, and
when the contents of the soonest treatment schedule for the one or more second samples have priority over the contents of the soonest treatment schedule for the one or more first samples, the control unit is configured to suspend the start of the soonest treatment for the one or more first samples using the horizontal direction movement unit.

20. The automatic tissue staining device according to claim 2, wherein:
one or more of the glass slides are situated in the second region,
the control unit is configured to judge whether or not a soonest treatment for one or more second samples on the one or more glass slides situated in the second region can be started,
when the soonest treatment for the one or more second samples can be started, the control unit is configured to make a comparison between contents of a soonest treatment schedule for one or more first samples on the one or more glass slides situated in the first region and contents of a soonest treatment schedule for the one or more second samples,
when the contents of the soonest treatment schedule for the one or more first samples have priority over the contents of the soonest treatment schedule for the one or more second samples, the control unit is configured to permit the start of the soonest treatment for the one or more first samples using the horizontal direction movement unit, and
when the contents of the soonest treatment schedule for the one or more second samples have priority over the contents of the soonest treatment schedule for the one or more first samples, the control unit is configured to suspend the start of the soonest treatment for the one or more first samples using the horizontal direction movement unit.

* * * * *